United States Patent
Minami et al.

(10) Patent No.: US 6,667,325 B1
(45) Date of Patent: Dec. 23, 2003

(54) SUBSTITUTED PYRAZOLE COMPOUNDS

(75) Inventors: Nobuyoshi Minami, Yokohama (JP); Michitaka Sato, Kawasaki (JP); Koichi Hasumi, Machida (JP); Norio Yamamoto, Kawasaki (JP); Katsuyuki Keino, Yokohama (JP); Teruaki Matsui, Kawasaki (JP); Arihiro Kanada, Kawasaki (JP); Shuji Ohta, Kawasaki (JP); Takahisa Saito, Kawasaki (JP); Shuichiro Sato, Kawasaki (JP); Akira Asagarasu, Machida (JP); Satoshi Doi, Kawasaki (JP); Motohiro Kobayashi, Kawasaki (JP); Jun Sato, Kawasaki (JP); Hajime Asano, Kawasaki (JP)

(73) Assignee: Teikoku Hormone Mfg. Co., Ltd., Tokyo (JP)

( * ) Notice: Subject to any disclaimer, the term of this patent is extended or adjusted under 35 U.S.C. 154(b) by 0 days.

(21) Appl. No.: 09/980,579

(22) PCT Filed: Jun. 1, 2000

(86) PCT No.: PCT/JP00/03547
§ 371 (c)(1),
(2), (4) Date: Dec. 3, 2001

(87) PCT Pub. No.: WO00/75131
PCT Pub. Date: Dec. 14, 2000

(30) Foreign Application Priority Data

Jun. 3, 1999 (JP) .......................... 11/156683
Jun. 3, 1999 (JP) .......................... 11/157011

(51) Int. Cl.⁷ ............... C07D 401/04; A61K 31/4439
(52) U.S. Cl. ............... 514/341; 514/333; 546/275.4; 546/256
(58) Field of Search .............. 546/275.4, 256; 514/341, 333

(56) References Cited

U.S. PATENT DOCUMENTS 6,087,381 A 7/2000 Hanson et al. .............. 514/341

FOREIGN PATENT DOCUMENTS

| WO | 95/31451 | 11/1995 |
|---|---|---|
| WO | 96/03385 | 2/1996 |
| WO | 98/52940 | 11/1998 |
| WO | 99/58523 | 11/1999 |
| WO | 00/31063 | 6/2000 |

OTHER PUBLICATIONS

CA 130: 38377, Anantanarayan et al. 1998.*

* cited by examiner

Primary Examiner—Jane Fan
(74) Attorney, Agent, or Firm—Wenderoth, Lind & Ponack, L.L.P.

(57) ABSTRACT

Substituted pyrazole compounds represented by formula (I), or salts thereof are disclosed, wherein $R^1$ is —CH(OH)—CH($R^4$)—(A)$_n$—Y, —CH$_2$—CH($R^4$)—(A)$_n$—Y, —CO—B$^1$—A—Y or the like (wherein A is a lower alkylene; Y is an aryl group which may be substituted, for example, by halogen, or the like; $R^4$ is a hydrogen atom or a lower alkyl group; $B^1$ is —CH($R^4$)— or —N($R^4$)—; and n is 0 or 1); $R^2$ is a hydrogen atom, a lower alkyl group which may be substituted by hydroxyl or the like, or an aralkyl group; $R^3$ is a phenyl group which may be substituted by halogen or the like, or a pyridyl group; and Q is a pyridyl or quinolyl group. These substituted pyrazole compounds or their salts have an excellent p38MAP kinase inhibiting effect and are hence useful in the prevention or treatment of tumor necrosis factor α-related diseases, interleukin 1-related diseases, interleukin 6-related diseases or cyclooxygenase II-related diseases.

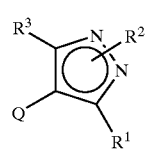

(I)

11 Claims, No Drawings

SUBSTITUTED PYRAZOLE COMPOUNDS

This application is a 371 of PCT/JP00/03546 filed Jun. 01, 2000 now WO 00/75131.

TECHNICAL FIELD

This invention relates to novel aminopyrazole derivatives or salts thereof. More particularly, it relates to substituted pyrazole compounds represented by the following formula, or salts thereof.

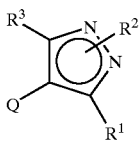
(I)

wherein:

$R^1$ represents a group of any one of the following formulae i) to viii):
- i) —CH(OH)—CH($R^4$)—(A)$_n$—Y
- ii) —CH=C($R^4$)—(A)$_n$—Y
- iii) —CH$_2$—CH($R^4$)—(A)$_n$—Y
- iv) —CO—$B^1$—A—Y
- v) —A—$B^2$—CH($R^4$)—Y
- vi) —A—CH($R^4$)—$B^2$—Y
- vii) —CH(OH)—CH=C($R^4$)—Y viii)

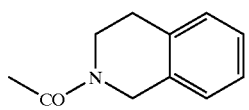

in which A is a lower alkylene group, Y is an aryl group (this aryl group may optionally be substituted by halogen, lower alkyl, lower alkoxy, amino or nitro), a cycloalkyl group or a heteroaryl group, $R^4$ is a hydrogen atom or a lower alkyl group, $B^1$ is —CH($R^4$)— or —N($R^4$)—, $B^2$ is —CH(OH)—, —CO— or —O—, and n is 0 or 1;

$R^2$ represents a hydrogen atom, a lower alkyl group [this lower alkyl group may optionally be substituted by hydroxyl, amino, or mono- or di-(lower alkyl)amino] or an aralkyl group;

$R^3$ represents a phenyl group (this phenyl group may optionally be substituted by halogen, trifluoromethyl or lower alkylenedioxy) or a pyridyl group; and Q represents a pyridyl or quinolyl group.

BACKGROUND ART

TNF-α, IL-1, IL-6 and COX-II are proteins which are predominantly produced by immunocompetent cells such as macrophages and neutrophilic leukocytes, and constitute important factors participating, for example, in immuno-regulatory functions and inflammatory symptoms. TNF-α and the like are also known as factors participating in many biological reactions in the hematopoietic system, the endocrine system, the nervous system and the like. Accordingly, the excessive or uncontrolled production of TNF-α and the like in the living body are believed to be closely related to the onset and aggravation of diseases associated with TNF-α and the like.

On the other hand, p38MAP kinase found within various types of cells in the living body are known to activate, in particular, some types of transcription factors. Specifically, transcription factors such as NF-κB, AP-1 and CREB bind to a certain DNA sequence common to TNF-α, IL-1, IL-6, COX-II and the like, and thereby promote transcription. Within the cell nucleus, these transcription factors are activated by the action of p38MAP kinase, so that proteins such as TNF-α are synthesized from the transcribed mRNA. The mRNA which has gone out of the nucleus in the presence of calcium is inactivated by binding to a protein having a specific sequence, and decomposed rapidly. However, in the presence of p38MAP kinase activated by phosphorylation, the mRNA is released from the protein and thereby activated. Consequently, it is believed that the synthesis of proteins such as TNF-α, IL-1, IL-6 and COX-II is also promoted along this pathway.

Accordingly, it is believed that the production of TNF-α, IL-1, IL-6, COX-II and the like can be hindered by inhibiting p38MAP kinase. On the basis of this concept, there have been proposed a number of compounds which have a p38MAP kinase inhibiting effect and thereby hinder the production of TNF-α, IL-1, IL-6, COX-II and the like (see, for example, Bioorganic & Medicinal Chemistry, Vol. 5, No. 1, pp. 49–64, 1997; and the Pamphlet of PCT International Publication WO93/14081).

It is expected that these TNF-α production inhibitors, IL-1 production inhibitors, IL-6 production inhibitors and COX-II production inhibitors will be effective in the treatment or prevention of TNF-α-related diseases, IL-1-related diseases, IL-6-related diseases and COX-II-related diseases, such as rheumatoid arthritis, multiple sclerosis, osteoarthritis, psoriasis, viral and bacterial infections, asthma, septic shock, IBD, Crohn's disease, Alzheimer's disease, diabetes, cachexia, osteoporosis, graft versus host disease, adult RDS, arteriosclerosis, gout, glomerulonephritis, congestive heart failure, ulcerative colitis, sepsis, cerebral malaria, restenosis, hepatitis, SLE, thrombosis, born resorption disease, chronic pulmonary inflammation disease, cardiac reperfusion injury, renal reperfusion injury, cancer, Reiter's syndrome, preterm labor, eczema, allograft rejection, stroke, fever, Behcet's disease, neuralgia, meningitis, sunburn, contact dermatitis, acute synovitis, spondylitis, muscle degeneration, angiogenesis, conjunctivitis, psoriatic arthritis, viral myocarditis, pancreatitis, glioblastoma, bleeding, joint inflammation, endotoxic shock, parasitic infections, tuberculosis, myocardial infarction, leprosy, diabetic retinopathy, IBS, transplant rejection, burns, bronchitis, ischemic heart disease, eclampsia, pneumonia, remission of swelling, low back pain, laryngopharyngitis, Kawasaki disease, myelopathy and atopic dermatitis.

Meanwhile, some types of pyrazole derivatives having a p38MAP kinase inhibiting effect have recently been proposed (see the Pamphlets of PCT International Publications WO98/52940 and WO98/52941).

The present inventors have now found that, among a series of pyrazole compounds in which the 5- and 3-position of the pyrazole ring is substituted by a phenyl or pyridyl group and the 4-position thereof is substituted by a pyridyl or quinolyl group, the compounds further having a certain substituent comprising an aryl, cycloalkyl or heteroaryl group attached to the 3- or 5-position of the pyrazole ring through the medium of a principal chain composed of at least two carbon, oxygen and/or nitrogen atoms have an excellent p38MAP kinase inhibiting effect and are hence exhibit an inhibitory effect on the production of TNF-α, IL-1, IL-6, COX-II and the like.

Thus, the present invention provides substituted pyrazole compounds represented by the above formula (I), or salts thereof.

DISCLOSURE OF THE INVENTION

The term "lower" as used herein means that the group or compound modified by this term has 6 or less carbon atoms and preferably 4 or less carbon atoms.

Thus, examples of the "lower alkyl group" include methyl, ethyl, n-propyl, isopropyl, n-butyl, isobutyl, sec-butyl, tert-butyl, n-pentyl and n-hexyl, and examples of the "lower alkoxy group" include methoxy, ethoxy, n-propoxy, isopropoxy, n-butoxy, isobutoxy, sec-butoxy and n-hexyloxy. Moreover, examples of the "lower alkylene group" include —$CH_2$—, —$CH(CH_3)$—, —$CH(C_2H_5)$—, —$(CH_2)_2$—, —$CH_2$—$CH(CH_3)$—, —$CH_2$—$CH(C_2H_5)$—, —$(CH_2)_3$—, —$CH_2$—$CH_2$—$CH(CH_3)$—, —$(CH_2)_4$— and —$(CH_2)_6$—, and examples of the "lower alkylenedioxy group" include methylenedioxy, ethylenedioxy and propylenedioxy.

The "aryl group" is a monocyclic or polycyclic aromatic hydrocarbon group, and examples thereof include phenyl, indenyl and naphthyl. The "aralkyl group" is an alkyl group substituted by an aryl group as defined above and preferably an aryl-substituted lower alkyl group, and examples thereof include benzyl, 1-phenylethyl, 2-phenylethyl, 1-phenypropyl, 3-phenylpropyl, 4-phenylbutyl, 1-naphthylmethyl, 2-naphthymethyl and diphenylmethyl.

The "aryl group (this aryl group may optionally be substituted by halogen, lower alkyl, lower alkoxy, amino or nitro)" represented by the symbol Y may preferably be an unsubstituted phenyl group; a phenyl group substituted by 1 or 2 substituents selected from halogen, lower alkyl, lower alkoxy, amino and nitro; or a phenyl group substituted by 3 to 5 halogen atoms.

Thus, these substituted aryl groups include, for example, 2-chlorophenyl, 3-chlorophenyl, 2-fluorophenyl, 4-fluorophenyl, 2-bromophenyl, 2-methylphenyl, 3-methylphenyl, 4-methylphenyl, 2-methoxyphenyl, 4-methoxyphenyl, 2-aminophenyl, 4-aminophenyl, 2-nitrophenyl, 4-nitrophenyl, 2,4-dichlorophenyl, 3,4-dichlorophenyl, 2,4-difluorophenyl, 2,5-difluorophenyl, 2,6-difluorophenyl, 2-chloro-4-fluorophenyl, 2,5-dimethylphenyl, 2,4-dimethoxyphenyl, 4-amino-3-methylphenyl, 3-methyl-4-nitrophenyl and 2,3,4,5,6-pentafluorophenyl.

The term "cycloalkyl group" generally comprehends cycloalkyl groups having 3 to 10 carbon atoms, and examples thereof include cyclopropyl, cyclobutyl, cyclopentyl, cyclohexyl, cycloheptyl and cyclooctyl.

The "heteroaryl group" may be a monocyclic or polycyclic unsaturated heterocyclic group which contains 1 to 4 heteroatoms selected from nitrogen, oxygen and sulfur atoms and, which includes a five- or six-membered ring. Alternatively, the heterocyclic ring may further be fused with a cyclic hydrocarbon group to form a fused ring. Among such heteroaryl groups, preferred ones are monocyclic or bicyclic unsaturated heterocyclic groups which contain 1 or 2 heteroatoms selected from nitrogen, oxygen and sulfur atoms, which include a five- or six-membered ring, and which may optionally be fused with a phenyl group. More preferred ones are monocyclic unsaturated heterocyclic groups which contain 1 or 2 heteroatoms selected from nitrogen, oxygen and sulfur atoms and comprise a five- or six-membered ring.

Thus, these "heteroaryl groups" include, for example, pyrrolyl, furyl, thienyl, imidazolyl, pirazolyl, oxazolyl, isoxazolyl, thiazolyl, triazolyl, thiadiazolyl, tetrazolyl, pyridyl, pyranyl, pyrimidinyl, pyridazinyl, pyrazinyl, azepinyl, azocinyl, purinyl, naphthidinyl, pteridinyl, benzothienyl, benzofuranyl, indolyl, isoindolyl, indazolyl, benzoxazolyl, benzothiazolyl, quinolyl, isoquinolyl, chromenyl, phthalazinyl, quinazolinyl, quinoxalinyl, carbazolyl, phenanthridinyl, acridinyl and dibenzazepinyl.

On the other hand, the term "halogen atom" comprehends fluorine, chlorine, bromine and iodine atoms.

The "lower alkyl group [this lower alkyl group may optionally be substituted by hydroxyl, amino, or mono- or di-(lower alkyl)amino] represented by the symbol $R^2$ may be, for example, an unsubstituted lower alkyl group or a lower alkyl group substituted by one substituent selected from hydroxyl, amino, methylamino, ethylamino, dimethylamino and diethylamino. Preferred examples thereof include methyl, ethyl, isopropyl, n-butyl, 2-hydroxyethyl, 3-hydroxypropyl, 2-aminoethyl, 4-aminobutyl, 2-dimethylaminoethyl, 2-diethylaminoethyl and 3-methylaminopropyl.

The "phenyl group (this phenyl group may optionally be substituted by halogen, trifluoromethyl or lower alkylenedioxy)" represented by the symbol $R^3$ may be, for example, an unsubstituted phenyl group or a phenyl group substituted by 1 or 2 substituents selected from halogen, trifluoromethyl and lower alkylenedioxy. Preferred examples thereof include phenyl, 3-fluorophenyl, 4-fluorophenyl, 3,4-difluorophenyl, 3-chlorophenyl, 3-chloro-4-fluorophenyl, 3-trifluoromethylphenyl, 3,4-methylenedioxyphenyl and 3,4-ethylenedioxyphenyl.

The "pyridyl group or quinolyl group" represented by the symbol Q may preferably be a 4-pyridyl or 4-quinolyl group.

One preferred class of compounds in accordance with the present invention are the compounds of formula (I) in which $R^1$ is a group of the formula —$CH_2$—$CH(R^4)$—$(A)_n$—Y.

Another preferred class of compounds in accordance with the present invention are the compounds of formula (I) in which A is —$CH_2$—, —$CH(CH)$— or —$(CH_2)_2$—.

Still another preferred class of compounds in accordance with the present invention are the compounds of formula (I) in which Y is phenyl, 2-chlorophenyl, 4-fluorophenyl, 2-methylphenyl, 3-methylphenyl, 2-methoxyphenyl, 4-methoxyphenyl, 2-aminophenyl, 4-aminophenyl, 2-nitrophenyl, 4-nitrophenyl, 2-chloro-4-fluorophenyl, 4-amino-3-methylphenyl, 3-methyl-4-nitrophenyl, 2,3,4,5,6-pentafluorophenyl, cyclohexyl, 1-pyrazolyl, 2-pyridyl, 3-pyridyl, 4-pyridyl or 5-pyrimidinyl.

A further preferred class of compounds in accordance with the present invention are the compounds of formula (I) in which $R^4$ is hydrogen or methyl.

Still a further preferred class of compounds in accordance with the present invention are the compounds of formula (I) in which $R^2$ is hydrogen, methyl, ethyl, n-propyl, isopropyl, 2-hydroxyethyl or 2-dimethylaminoethyl.

Still a further preferred class of compounds in accordance with the present invention are the compounds of formula (I) in which $R^3$ is 3-chlorophenyl, 4-fluorophenyl, 3-trifluoromethylphenyl, 3,4-dichlorophenyl, 3,4-difluorophenyl, 3-chloro-4-fluorophenyl, 3,4-methylenedioxyphenyl, 2-pyridyl, 3-pyridyl or 4-pyridyl.

Still a further preferred class of compounds in accordance with the present invention are the compounds of formula (I) in which Q is 4-pyridyl.

Where $R^2$ represents a hydrogen atom in the compounds of the above formula (I) in accordance with the present invention, such hydrogen atoms are usually attached to one of the two nitrogen atoms constituting the pyrazole ring, at a certain ratio depending on the reaction conditions and the like. Consequently, the position of substitution by $R^2$ cannot be specified. Accordingly, the representation of the position of the substituent $R^2$ as used in the chemical structural formula given herein means that "where $R^2$ represents a hydrogen atom, it is unknown which of the two nitrogen atoms constituting the pyrazole ring $R^2$ is attached to." Where $R^2$ represents a group other than a hydrogen atom, the position of substitution by $R^2$ can be specified. Accordingly, the above-described representation means that "where $R^2$ represents a group other than a hydrogen atom, $R^2$ is attached to a fixed one of the two nitrogen atoms constituting the pyrazole ring."

Thus, where $R^2$ represents a hydrogen atom, it cannot be determined which of the 3- and 5-positions the substituents $R^1$ and $R^3$ are attached to. Accordingly, in the notation of compounds in the examples and elsewhere, the positions of substitution by $R^1$ and $R^3$ are represented by "3(5)-" or "5(3)-".

In addition to the compounds described in the examples which will be given later, typical examples of the compounds of the above formula (I) which are provided by the present invention are as follows.

The compounds of formula (I) in which $R^1$ is a group of formula i) include:

3(5)-(4-fluorophenyl)-5(3)-(1-hydroxy-5-phenylpentyl)-4-(4-pyridyl)pyrazole,

3(5)-(4-fluorophenyl)-5(3)-[1-hydroxy-3-(1-naphthyl)propyl]-4-(4-pyridyl)pyrazole, 3(5)-(4-fluorophenyl)-5(3)-[1-hydroxy-3-(4-tolyl)propyl]-4-(4-pyridyl)pyrazole, 5(3)-[3-(3-chlorophenyl)-1-hydroxypentyl]-3(5)-(4-fluorophenyl)-4-(4-pyridyl)pyrazole, 5(3)-[3-(2,4-difluorophenyl)-1-hydroxypropyl]-3(5)-(4-fluorophenyl)-4-(4-pyridyl)pyrazole, 5(3)-[3-(3,4-dichlorophenyl)-1-hydroxypropyl]-3(5)-(4-fluorophenyl)-4-(4-pyridyl)pyrazole, 3(5)-(4-fluorophenyl)-5(3)-[1-hydroxy-3-(2-methoxyphenyl)-propyl]-4-4-(4-pyridyl)pyrazole, 3(5)-(4-fluorophenyl)-5(3)-[1-hydroxy-3-(3-tolyl)butyl]-4-(4-pyridyl)pyrazole, 5(3)-(3-cyclohexyl-1-hydroxybutyl)-3(5)-(4-fluorophenyl)-4-(4-pyridyl)pyrazole, 3(5)-(4-fluorophenyl)-5(3)-[1-hydroxy-3-(2-pyridyl)propyl]-4-(4-pyridyl)pyrazole, 3(5)-(4-fluorophenyl)-5(3)-[1-hydroxy-3-(4-pyridyl)propyl]-4-(4-pyridyl)pyrazole, 3(5)-(4-fluorophenyl)-5(3)-[1-hydroxy-3-(3-pyridyl)butyl]-4-(4-pyridyl)pyrazole, 3(5)-(4-fluorophenyl)-5(3)-[1-hydroxy-4-(3-pyridyl)butyl]-4-(4-pyridyl)pyrazole, 3(5)-(4-fluorophenyl)-5(3)-[1-hydroxy-3-(3-thienyl)propyl]-4-(4-pyridyl)pyrazole, 3(5)-(4-fluorophenyl)-5(3)-[3-(2-furyl)-1-hydroxypropyl]-4-(4-pyridyl)pyrazole, 3(5)-(4-fluorophenyl)-5(3)-[1-hydroxy-3-(3-pyranyl)propyl]-4-(4-pyridyl)pyrazole, 3(5)-(4-fluorophenyl)-5(3)-[1-hydroxy-3-(4-pyridazinyl)propyl]-4-(4-pyridyl)pyrazole, 3-(4-fluorophenyl)-5-(1-hydroxy-4-phenylbutyl)-1-methyl-4-(4-pyridyl)pyrazole, 3-(4-fluorophenyl)-5-(1-hydroxy-2-methyl-3-phenylpropyl)-1-methyl-4-(4-pyridyl)pyrazole, 3-(4-fluorophenyl)-5-(1-hydroxy-3-phenylbutyl)-1-methyl-4-(4-pyridyl)pyrazole, 3-(4-fluorophenyl)-5-[1-hydroxy-3-(3-tolyl)propyl]-1-methyl-4-(4-pyridyl)pyrazole, 5-(3-cyclohexyl-1-hydroxypropyl)-3-(4-fluorophenyl)-1-methyl-4-(4-pyridyl)pyrazole, 1-ethyl-3-(4-fluorophenyl)-5-(1-hydroxy-3-phenylpropyl)-4-(4-pyridyl)pyrazole, 3-(4-fluorophenyl)-5-(1-hydroxy-3-phenylpropyl)-1-isopropyl-4-(4-pyridyl)pyrazole, 3-(4-fluorophenyl)-1-(2-hydroxyethyl)-5-(1-hydroxy-3-phenylpropyl)-4-(4-pyridyl)pyrazole, 3-(4-fluorophenyl)-5-(1-hydroxy-3-phenylpropyl)-1-(3-phenylpropyl)-4-(4-pyridyl)pyrazole, 3(5)-(3-chlorophenyl)-5(3)-(1-hydroxy-3-phenylpropyl)-4-(4-pyridyl)pyrazole, 3(5)-(3,4-difluorophenyl)-5(3)-(1-hydroxy-3-phenylpropyl)-4-(4-pyridyl)pyrazole, 3-(3,4-difluorophenyl)-5-(1-hydroxy-3-phenylpropyl)-1-methyl-4-(4-pyridyl)pyrazole, 3(5)-phenyl-5(3)-(1-hydroxy-3-phenylpropyl)-4-(4-pyridyl)pyrazole, and the like.

The compounds of formula (I) in which $R^1$ is a group of formula ii) include:

3(5)-(4-fluorophenyl)-5(3)-(2-methyl-3-phenyl-1-propenyl)-4-(4-pyridyl)pyrazole, 5(3)-[3-(3-chlorophenyl)-1-propenyl]-3(5)-(4-fluorophenyl)-4-(4-pyridyl)pyrazole, 5(3)-(3-cyclohexyl-1-propenyl)-3(5)-(4-fluorophenyl)-4-(4-pyridyl)pyrazole, 3(5)-(4-fluorophenyl)-4-(4-pyridyl)-5(3)-[3-(4-pyridyl)-1-propenyl]pyrazole, 3(5)-(4-fluorophenyl)-4-(4-pyridyl)-5(3)-[3-(3-pyridyl)-1-butenyl]pyrazole, 3(5)-(4-fluorophenyl)-5(3)-[2-methyl-3-(3-pyridyl)-1-propenyl]-4-(4-pyridyl)pyrazole, 3(5)-(4-fluorophenyl)-4-(4-pyridyl)-5(3)-[3-(3-thienyl)-1-propenyl]pyrazole, 3(5)-(4-fluorophenyl)-4-(4-pyridyl)-5(3)-[3-(5-pyrimidinyl)-1-propenyl]pyrazole, 3-(4-fluorophenyl)-1-methyl-5-(2-methyl-3-phenyl-1-propenyl]-4-(4-pyridyl)pyrazole, 5(3)-(3-phenyl-1-propenyl)-3(5)-(2-pyridyl)-4-(4-pyridyl)pyrazole, and the like.

The compounds of formula (I) in which $R^1$ is a group of formula iii) include:

3(5)-(4-fluorophenyl)-5(3)-(4-phenylpentyl)-4-(4-pyridyl)pyrazole,

3(5)-(4-fluorophenyl)-5(3)-(5-phenylpentyl)-4-(4-pyridyl)pyrazole,

3(5)-(4-fluorophenyl)-5(3)-[3-(1-naphthyl)propyl]-4-(4-pyridyl)pyrazole,

3(5)-(4-fluorophenyl)-5(3)-[3-(2-naphthyl)propyl]-4-(4-pyridyl)pyrazole,

5(3)-[3-(2-chloro-4-methylphenyl)propyl]-3(5)-(4-fluorophenyl)-4-(4-pyridyl)pyrazole, 5(3)-[3-(3-chlorophenyl)propyl]-3(5)-(4-fluorophenyl)-4-(4-pyridyl)pyrazole, 5(3)-[3-(2,5-difluorophenyl)propyl]-3(5)-(4-fluorophenyl)-4-(4-pyridyl)pyrazole, 5(3)-[3-(2,6-difluorophenyl)propyl]-3(5)-(4-fluorophenyl)-4-(4-pyridyl)pyrazole, 3(5)-(4-fluorophenyl)-5(3)-[3-(2-methoxyphenyl)propyl]-4-(4-pyridyl)pyrazole, 3(5)-(4-fluorophenyl)-4-(4-pyridyl)-5(3)-[3-(3-tolyl)butyl]pyrazole, 3(5)-(4-fluorophenyl)-5(3)-(3-pentafluorophenylpropyl)-4-(4-pyridyl)pyrazole, 5(3)-(3-cyclohexylpropyl)-3(5)-(4-fluorophenyl)-4-(4-pyridyl)pyrazole, 3(5)-(4-fluorophenyl)-4-(4-pyridyl)-5(3)-[4-(3-pyridyl)butyl]pyrazole, 3(5)-(4-fluorophenyl)-4-(4-pyridyl)-5(3)-[3-(3-thienyl)propyl]pyrazole, 3(5)-(4-fluorophenyl)-5(3)-[3-(2-furyl)propyl]-4-(4-pyridyl)pyrazole, 3(5)-(4-fluorophenyl)-5(3)-[3-(3-pyranyl)propyl]-4-(4-pyridyl)pyrazole, 3(5)-(4-fluorophenyl)-5(3)-[3-(4-pyridazinyl)propyl]-4-(4-pyridyl)pyrazole, 3-(4-fluorophenyl)-1-methyl-5-(4-phenylbutyl)-4-(4-pyridyl)pyrazole, 3-(4-fluorophenyl)-1-methyl-5-(3-phenylbutyl)-4-(4-pyridyl)pyrazole, 3-(4-fluorophenyl)-1-methyl-5-(2-methyl-3-phenylbutyl)-4-(4-pyridyl)pyrazole, 3-(4-fluorophenyl)-1-methyl-4-(4-pyridyl)-5-[3-(tolyl)propyl]pyrazole, 3-(4-fluorophenyl)-1-methyl-5-[3-(2-nitrophenyl)propyl]-4-(4-pyridyl)pyrazole, 3-(4-fluorophenyl)-1-methyl-5-[3-(4-nitrophenyl)propyl]-4-(4-pyridyl)pyrazole, 5-(3-cyclohexylpropyl)-3-(4-fluorophenyl)-1-methyl-4-(4-pyridyl)pyrazole, 1-ethyl-3-(4-fluorophenyl)-5-(3-phenylpropyl)-4-(4-pyridyl)pyrazole, 3-(4-fluorophenyl)-1-isopropyl-5-(3-phenylpropyl)-4-(4-pyridyl)pyrazole, 3-(4-fluorophenyl)-1,5-bis(3-phenylpropyl)-4-(4-pyridyl)pyrazole, 3(5)-(3-chlorophenyl)-5(3)-(3-phenylpropyl)-4-(4-pyridyl)pyrazole, 5(3)-(3-phenylpropyl)-4-(4-pyridyl)-3(5)-(3-trifluoromethylphenyl)pyrazole, 3(5)-(3,4-difluorophenyl)-5(3)-(3-phenylpropyl)-4-(4-pyridyl)pyrazole, 3(5)-(3-chloro-4-fluorophenyl)-5(3)-(3-phenylpropyl)-4-(4-pyridyl)pyrazole, 3(5)-(3,4-dichlorophenyl)-5(3)-(3-phenylpropyl)-4-(4-pyridyl)pyrazole, 5(3)-[3-(2-chloro-4-fluorophenyl)propyl]-3(5)-(2-pyridyl)-4-(4-pyridyl)pyrazole, 5(3)-(3-phenylpropyl)-3(5),4-di(4-pyridyl)pyrazole, 3(5)-phenyl-5(3)-(3-phenylpropyl)-4-(4-pyridyl)pyrazole, 3-(3,4-difluorophenyl)-1-methyl-5-(3-phenylpropyl)-4-(4-pyridyl)pyrazole, 3-(3-chloro-4-fluorophenyl)-1-methyl-5-(3-phenylpropyl)-4-(4-pyridyl)pyrazole, 3-(3,4-dichlorophenyl)-1-methyl-5-(3-phenylpropyl)-4-(4-pyridyl)pyrazole, 3(5)-(4-fluorophenyl)-5(3)-[3-(3-pyridyl)propyl]-4-(4-quinolyl)-pyrazole, and the like.

The compounds of formula (I) in which $R^1$ is a group of formula iv) include:

3(5)-(4-fluorophenyl)-5(3)-(4-phenylbutyryl)-4-(4-pyridyl)pyrazole,

3(5)-(4-fluorophenyl)-5(3)-(3-phenylbutyryl)-4-(4-pyridyl)pyrazole,

3(5)-(4-fluorophenyl)-4-(4-pyridyl)-5(3)-[3-(3-pyridyl)propionyl]pyrazole,

3(5)-(4-fluorophenyl)-4-(4-pyridyl)-5(3)-[3-(3-pyrimidinyl)propionyl]pyrazole, 3-(4-fluorophenyl)-1-methyl-5-(2-methyl-3-phenylpropionyl)-4-(4-pyridyl)pyrazole, 3(5)-(4-fluorophenyl)-5(3)-(2-methylbenzylaminocarbonyl)-4-(4-pyridyl)pyrazole, 5(3)-(3-chlorobenzylaminocarbonyl)-3(5)-(4-fluorophenyl)-4-(4-pyridyl)pyrazole, 5(3)-(4-fluorobenzylaminocarbonyl)-3(5)-(4-fluorophenyl)-4-(4-pyridyl)pyrazole, 3(5)-(4-fluorophenyl)-5(3)-(2-methoxybenzylaminocarbonyl)-4-(4-pyridyl)pyrazole, 3(5)-(4-fluorophenyl)-5(3)-(4-methoxybenzylaminocarbonyl)-4-(4-pyridyl)pyrazole, 3(5)-(4-fluorophenyl)-4-(4-pyridyl)-5(3)-(2-pyridylmethylaminocarbonyl)pyrazole, 3(5)-(4-fluorophenyl)-4-(4-pyridyl)-5(3)-(3-pyridylmethylaminocarbonyl)pyrazole, 5-benzylaminocarbonyl-3-(4-fluorophenyl)-1-methyl-4-(4-pyridyl)pyrazole, 3-(4-fluorophenyl)-1-methyl-5-(1-phenethylaminocarbonyl)-4-(4-pyridyl)pyrazole, 5-(4-fluorobenzylaminocarbonyl)-3-(4-fluorophenyl)-1-methyl-4-(4-pyridyl)pyrazole, 5-(2-chlorobenzylaminocarbonyl)-3-(4-fluorophenyl)-1-methyl-4-(4-pyridyl)pyrazole, 3-(4-fluorophenyl)-5-(2-methoxybenzylaminocarbonyl)-1-methyl-4-(4-pyridyl)pyrazole, 3-(4-fluorophenyl)-1-methyl-4-(4-pyridyl)-5-(2-pyridylmethylaminocarbonyl)pyrazole, 5-benzylaminocarbonyl-1-ethyl-3-(4-fluorophenyl)-4-(4-pyridyl)pyrazole, 1-ethyl-3-(4-fluorophenyl)-4-(4-pyridyl)-5-(2-pyridylmethylaminocarbonyl)pyrazole, 5-benzylaminocarbonyl-3-(4-fluorophenyl)-1-(n-propyl)-4-(4-pyridyl)pyrazole, 5-benzylaminocarbonyl-3-(4-fluorophenyl)-1-isopropyl-4-(4-pyridyl)pyrazole, 5-benzylaminocarbonyl-3-(4-fluorophenyl)-1-(2-hydroxyethyl)-4-(4-pyridyl)pyrazole, 3-(4-fluorophenyl)-1-methyl-5-(N-methyl-2-chlorobenzylaminocarbonyl)-4-(4-pyridyl)pyrazole, 3-(4-fluorophenyl)-1-methyl-5-(N-methyl-2-methoxybenzylaminocarbonyl)-4-(4-pyridyl)pyrazole, 5-(N,3-dimethyl-4-nitrobenzylaminocarbonyl)-3-(4-fluorophenyl)-1-methyl-4-(4-pyridyl)pyrazole, 5-(N,3-dimethyl-4-aminobenzylaminocarbonyl)-3-(4-fluorophenyl)-1-methyl-4-(4-pyridyl)pyrazole, 3-(4-fluorophenyl)-1-methyl-5-(N-methyl-2-pyridylmethylaminocarbonyl)-4-(4-pyridyl)pyrazole, 1-ethyl-5-(N-ethyl-2-pyridylmethylaminocarbonyl)-3-(4-fluorophenyl)-4-(4-pyridyl)pyrazole, 3-(4-fluorophenyl)-5-(N-methylbenzylaminocarbonyl)-1-(n-propyl)-4-(4-pyridyl)pyrazole, 5-(N-ethylbenzylaminocarbonyl)-3-(4-fluorophenyl)-1-(n-propyl)-4-(4-pyridyl)pyrazole, and the like.

The compounds of formula (I) in which $R^1$ is a group of formula v) include:

3-(4-fluorophenyl)-5-(2-hydroxy-3-phenylpropyl)-1-methyl-4-(4-pyridyl)pyrazole,

3(5)-(4-fluorophenyl)-5(3)-(1-phenylethyloxymethyl)-4-(4-pyridyl)pyrazole,

3(5)-(4-fluorophenyl)-5(3)-[1-(1-phenylethyloxy)ethyl]-4-(4-pyridyl)pyrazole,

5(3)-(2-chlorobenzyloxymethyl)-3(5)-(4-fluorophenyl)-4-(4-pyridyl)pyrazole, 5-benzyloxymethyl-3-(4-fluorophenyl)-1-methyl-4-(4-pyridyl)pyrazole, 3-(4-fluorophenyl)-1-methyl-5-(1-phenylethyloxymethyl)-4-(4-pyridyl)pyrazole, and the like.

The compounds of formula (I) in which $R^1$ is a group of formula vi) include:

3(5)-(4-fluorophenyl)-5(3)-(2-phenoxypropyl)-4-(4-pyridyl)pyrazole,

3(5)-(4-fluorophenyl)-5(3)-(3-phenoxypropyl)-4-(4-pyridyl)pyrazole,

3(5)-(4-fluorophenyl)-4-(4-pyridyl)-5(3)-[2-(3-tolyloxy)ethyl]pyrazole,

5(3)-[2-(3-chlorophenoxy)ethyl]-3(5)-(4-fluorophenyl)-4-(4-pyridyl)pyrazole,

5(3)-[2-(3-fluorophenoxy)ethyl]-3(5)-(4-fluorophenyl)-4-(4-pyridyl)pyrazole,

5(3)-(2-cyclohexyloxyethyl)-3(5)-(4-fluorophenyl)-4-(4-pyridyl)pyrazole,

3(5)-(4-fluorophenyl)-4-(4-pyridyl)-5(3)-[2-(3-pyridyloxy)ethyl]pyrazole,

3(5)-(4-fluorophenyl)-4-(4-pyridyl)-5(3)-[2-(4-pyridyloxy)ethyl]pyrazole,

3(5)-(4-fluorophenyl)-4-(4-pyridyl)-5(3)-[2-(5-pyrimidinyloxy)ethyl]pyrazole,

3(5)-(4-fluorophenyl)-5(3)-(2-methyl-3-oxo-3-phenylpropyl)-4-(4-pyridyl)pyrazole, 3(5)-(4-fluorophenyl)-5(3)-(4-oxo-4-phenylbutyl)-4-(4-pyridyl)pyrazole, 3(5)-(4-fluorophenyl)-5(3)-[3-oxo-3-(3-pyridyl)propyl]-4-(4-pyridyl)pyrazole, 3-(4-fluorophenyl)-1-methyl-5-(3-oxo-3-phenylpropyl)-4-(4-pyridyl)pyrazole, 3-(4-fluorophenyl)-5-(3-hydroxy-3-phenylpropyl)-1-methyl-4-(4-pyridyl)pyrazole, and the like.

The compounds of formula (I) in which $R^1$ is a group of formula vii) include:

3(5)-(4-fluorophenyl)-5(3)-(1-hydroxy-3-phenyl-2-propenyl)-4-(4-pyridyl)pyrazole, 3(5)-(4-fluorophenyl)-5(3)-[1-hydroxy-3-(2-pyridyl)-2-propenyl]-4-(4-pyridyl)pyrazole, 3-(4-fluorophenyl)-5-(1-hydroxy-3-phenyl-2-propenyl)-1-methyl-4-(4-pyridyl)pyrazole, and the like.

The compounds of formula (I) in which $R^1$ is a group of formula viii) include:

3-(4-fluorophenyl)-1-methyl-4-(4-pyridyl)-5-[N-(1,2,3,4-tetrahydroisoquinolinyl)carbonyl]pyrazole, and the like.

The compounds of formula (I) in accordance with the present invention can form salts. Examples of such salts include salts formed with inorganic acids such as hydrochloric acid, hydrobromic acid, sulfuric acid, nitric acid and phosphoric acid; and salts formed with organic acids such as acetic acid, oxalic acid, citric acid, lactic acid, tartaric acid and p-toluenesulfonic acid. Among others, pharmaceutically acceptable salts are preferred.

According to the present invention, depending on the types of the substituents represented by $R^1$ and $R^2$, the compounds of the above formula (I) may be prepared, for example, by any of the processes (a) to (j) described below.

Process (a): The compounds of the above formula (I) in which $R^2$ is a hydrogen atom and $R^1$ is a group of formula i) may be prepared by:

(i) reacting an amino compound of the formula

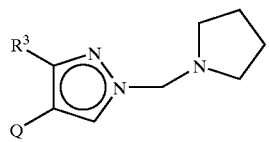

(II)

wherein $R^3$ and Q have the above-defined meanings, with an aldehyde compound of the formula

HOC—CH(R⁴)—(A)ₙ—Y    (III)

wherein $R^4$, A, n and Y have the above-defined meanings.

Process (b): The compounds of the above formula (I) in which $R^2$ is a hydrogen atom and $R^1$ is a group of formula ii) may be prepared by subjecting a compound of formula (I) in which $R^1$ is a group of formula i), to a dehydration reaction.

Process c): The compounds of the above formula (I) in which $R^2$ is a hydrogen atom and $R^1$ is a group of formula iii) may be prepared by:

(c-1) subjecting a compound of formula (I) in which $R^1$ is a group of formula ii), to a reduction reaction; or (c-2) reacting an ethanone compound of the formula

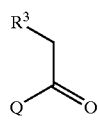

(IV)

wherein $R^3$ and Q have the above-defined meanings, with an imide ester compound of the formula

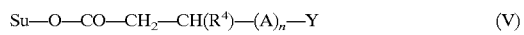

Su—O—CO—CH₂—CH(R⁴)—(A)ₙ—Y    (V)

wherein Su represents a succinimide group, and $R^4$, A, n and Y have the above-defined meanings, and reacting the resulting compound of the formula

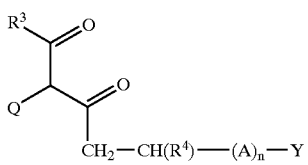

wherein $R^3$, $R^4$, A, n, Y and Q have the above-defined meanings, with hydrazine or a hydrate thereof.

Process (d): The compounds of the above formula (I) in which $R^2$ is a hydrogen atom, $R^1$ is a group of formula iv), and $B^1$ is —CH($R^4$)— may be prepared by subjecting a compound of formula (I) in which $R^1$ is a group of formula i) and n is 1, to an oxidation reaction.

Process (e): The compounds of the above formula (I) in which $R^2$ is a hydrogen atom, $R^1$ is a group of formula iv), and $B^1$ is —CH($R^4$)— may be prepared by reacting a carboxy compound of the formula

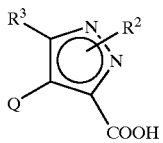

wherein $R^2$, $R^3$ and Q have the above-defined meanings, with an amino compound of the formula $$NH(R^4)-A-Y \qquad (VIII)$$

wherein $R^4$, A and Y have the above-defined meanings.

Process f): The compounds of the above formula (I) in which $R^2$ is a hydrogen atom and $R^1$ is a group of formula v) may be prepared by reacting an ethanone compound of formula (IV) with an imide ester compound of the formula

wherein $B^{21}$ is a protected hydroxymethylene group, a protected carbonyl group or —O—, and Su, $R^4$, A and Y have the above-defined meanings; reacting the resulting compound of the formula

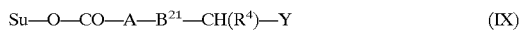

wherein $R^3$, $R^4$, A, $B^{21}$, Y and Q have the above-defined meanings, with hydrazine or a hydrate thereof; when $B^{21}$ in the resulting compound represents a protected hydroxymethylene group or a protected carbonyl group, eliminating the protecting group as required; and, when $B^1$ in the resulting compound represents —CO—, reducing the compound as required.

Process (g): The compounds of the above formula (I) in which $R^2$ is a hydrogen atom and $R^1$ is a group of formula vi) may be prepared by reacting a compound of the above formula (II) with a bromo compound of the formula

wherein A, $R^4$, $B^2$ and Y have the above-defined meanings.

Process (h): The compounds of the above formula (I) in which $R^2$ is a hydrogen atom and $R^1$ is a group of formula vii) may be prepared by reacting a compound of the above formula (II) with an aldehyde compound of the formula

wherein $R^4$ and Y have the above-defined meanings.

Process (i): The compounds of the above formula (I) in which $R^2$ is a hydrogen atom and $R^1$ is a group of formula viii) may be prepared by reacting a carboxy compound of formula (VII) with 1,2,3,4-tetrahydroisoquinoline.

Process (j): The compounds of the above formula (I) in which $R^2$ is an optionally substituted lower alkyl group or an aralkyl group may be prepared by treating a compound of formula (I) in which $R^2$ is a hydrogen atom, with a lower alkyl halide or an aralkyl halide.

In the above-described process (a), the reaction of a compound of formula (II) with an aldehyde compound of formula (III) may generally be carried out in an inert organic solvent selected, for example, from ethers such as tetrahydrofuran, dioxane and dimethoxyethane; and aromatic hydrocarbons such as benzene and toluene. Usually, the compound of formula (II) is first treated with a strong base such as n-butyl lithium, tert-butyl lithium, potassium tert-butoxide, lithium diisopropylamide or lithium bis(trimethylsilyl)amide, and then reacted with the aldehyde compound of formula (III). As to the reaction temperature, it is usually preferable to carry out the treatment with the strong base at a temperature of about −65° C. or below, and it is usually suitable to carry out the subsequent reaction with the aldehyde compound of formula (III) at a temperature ranging from an ice-cold temperature to room temperature.

The proportion of the aldehyde compound of formula (III) to the compound of formula (II) may generally be such that the aldehyde compound of formula (III) is used in an amount of at least 1 mole, preferably 1 to 2 moles, and more preferably 1.05 to 1.5 moles, per mole of the compound of formula (II). The strong base may generally be used in an amount of at least 1 mole, preferably 1 to 2 moles, and more preferably 1.05 to 1.5 moles, per mole of the compound of formula (II).

In the above-described process (b), the dehydration reaction of a compound of formula (I) in which $R^1$ is a group of formula i), namely a compound of the following formula (I-1)

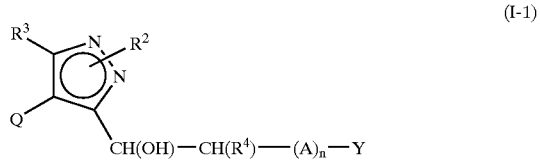

wherein $R^2$, $R^3$, $R^4$, A, n, Y and Q have the above-defined meanings, may generally be carried out in an inert organic solvent selected, for example, from aromatic hydrocarbons such as benzene, toluene and xylene; and sulfoxides such as dimethyl sulfoxide, optionally with the aid of a dehydrating agent such as 4-toluenesulfonic acid or camphorsulfonic acid. As the reaction temperature, it is usually suitable to employ a temperature ranging from room temperature to the reflux temperature of the reaction mixture and preferably from about 50° C. to the reflux temperature of the reaction mixture.

When a dehydrating agent is used in the dehydration reaction, the proportion of the dehydration agent to the compound of formula (I-1) may generally be such that the dehydrating agent is used in an amount of at least 1 mole, preferably 1.1 to 5 moles, and more preferably 1.5 to 3 moles, per mole of the compound of formula (I-1).

In the above-described process (c-1), the reduction reaction of a compound of formula (I) in which $R^1$ is a group of formula ii), namely a compound of the following formula (I-2)

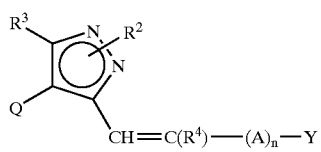

(I-2)

wherein $R^2$, $R^3$, $R^4$, A, n, Y and Q have the above-defined meanings, may generally be carried out by hydrogenating the compound at atmospheric pressure or elevated pressure in a solvent selected, for example, from alcohols such as methanol, ethanol and isopropanol; ethers such as tetrahydrofuran, dioxane and dimethoxyethane; and esters such as ethyl acetate, and in the presence of a catalyst such a palladium-carbon, hydrogenated palladium-carbon or Raney nickel. As the reaction temperature, it is usually suitable to employ a temperature in the range of 0° C. to 60° C. and preferably in the vicinity of room temperature.

In the above-described process (c-2), the reaction of an ethanone compound of formula (IV) with an imide ester compound of formula (V) may generally be carried out in an inert organic solvent selected, for example, from ethers such as tetrahydrofuran, dioxane and dimethoxyethane; and aromatic hydrocarbons such as benzene and toluene. Specifically, the ethanone compound of formula (IV) is first treated with a strong base such as sodium tert-butoxide, potassium tert-butoxide, tert-butyl lithium, n-butyl lithium, lithium diisopropylamide or lithium bis(trimethylsilyl) amide, and then reacted with the imide ester compound of formula (V). As to the reaction temperature, it is usually preferable to carry out the treatment with the strong base at a temperature of about −65° C. or below, and it is usually suitable to carry out the subsequent reaction with the imide ester compound of formula (V) at a temperature ranging from an ice-cold temperature to room temperature.

The proportion of the imide ester compound of formula (V) to the ethanone compound of formula (IV) may generally be such that the imide ester compound of formula (V) is used in an amount of at least 1 mole, preferably 1 to 5 moles, and more preferably 1.5 to 2.0 moles, per mole of the ethanone compound of formula (IV).

The resulting compound of formula (VI) may subsequently be reacted with hydrazine or a hydrate thereof and thereby converted to a compound of formula (I) which is desired in the present invention, namely a compound of formula (I) in which $R^2$ is a hydrogen atom and $R^1$ is a group of formula iii).

The reaction of the compound of formula (VI) with hydrazine or a hydrate thereof may generally be carried out in an inert solvent selected, for example, from water; ethers such as tetrahydrofuran, dioxane and diethyl ether; and alcohols such as methanol, ethanol and propanol. As the reaction temperature, it is usually suitable to employ a temperature ranging from an ice-cold temperature to about 50° C. and preferably in the vicinity of room temperature.

In the above-described process (d), the oxidation reaction of a compound of formula (I) in which $R^1$ is a group of formula i) and n is 1, namely a compound of the following formula (I-1-1)

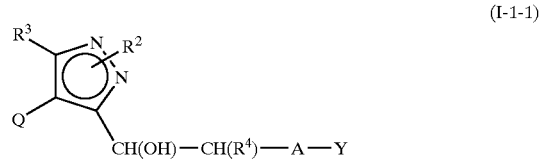

(I-1-1)

wherein $R^2$, $R^3$, $R^4$, A, Y and Q have the above-defined meanings, may generally be carried out by treating the compound with an oxidizing agent such as a combination of 2,2,6,6-tetramethyl-1-piperidyloxy radical and sodium hypochlorite; a combination of oxalyl chloride, dimethyl sulfoxide and trimethylamine; pyridinium chlorochromate; or pyridinium dichromate, in an inert organic solvent selected, for example, from halogenated hydrocarbons such as dichloromethane and chloroform. As the reaction temperature, it is usually suitable to employ a temperature ranging approximately from −20° C. to room temperature and preferably from −10° C. to an ice-cold temperature.

In this oxidation reaction, the proportion of the oxidizing agent to the compound of formula (I-1-1) may generally be such that the oxidizing agent is used in an amount of at least 1 mole, preferably 1 to 6 moles, and more preferably 1 to 2 moles, per mole of the compound of formula (I-1-1).

In the above-described process (e), the reaction of a carboxy compound of formula (VII) with an amino compound of formula (VIII) may generally be carried out in an inert organic solvent selected, for example, from amides such as dimethylformamide and dimethylacetamide; and halogenated hydrocarbons such as dichloromethane and chloroform. Specifically, this can be done by first converting the carboxy compound of formula (VII) to its reactive derivative (e.g., its N-hydroxysuccinimide ester, pentafluorophenyl ester, or p-nitrophenyl ester) and then reacting this derivative with the amino compound of formula (VIII); or by reacting the carboxy compound of formula (VII) with the amino compound of formula (VIII) in the presence of a condensing agent such as dicyclohexylcarbodiimide (DCC), water-soluble carbodiimide (WSC), diethyl cyanophosphate (DEPC) or diphenylphosphoryl azide (DPPA). As the reaction temperature, it is usually suitable to employ a temperature ranging from an ice-cold temperature to room temperature.

The proportion of the amino compound of formula (VIII) to the carboxy compound of formula (VII) may generally be such that the amino compound of formula (VIII) is used in an amount of at least 1 mole, preferably 1 to 2 moles, and more preferably 1 to 1.5 moles, per mole of the carboxy compound of formula (VII).

In the above-described process (f), the reaction of an ethanone compound of formula (IV) with an imide ester compound of formula (IX), and the subsequent reaction with hydrazine or a hydrate thereof may be carried out in the same manner as described above in connection with the process (c-2). When $B^{21}$ in the resulting compound represents a protected hydroxymethylene group or a protected carbonyl group, the protecting group may be eliminated in the usual manner, for example, by using a hydrolysis reaction, a catalytic hydrogenolysis reaction or the like according to the type of the protecting group.

When $B^2$ in the resulting compound represents —CO—, the compound may be reduced, for example, with the aid of a complex metal hydride such as lithium aluminum hydride.

In the above-described process (g), the reaction of a compound of formula (II) with a bromo compound of formula (XI) may generally be carried out in an inert organic solvent selected, for example, from ethers such as tetrahydrofuran, dioxane and dimethoxyethane; and aromatic hydrocarbons such as benzene and toluene. Usually, the compound of formula (II) is first treated with a strong base such as n-butyl lithium, tert-butyl lithium, potassium tert-butoxide, lithium diisopropylamide or lithium bis(trimethylsilyl)amide, and then reacted with the bromo compound of formula (XI). As to the reaction temperature, it is usually preferable to carry out the treatment with the strong base at a temperature of about −65° C. or below, and it is usually suitable to carry out the subsequent reaction with the bromo compound of formula (XI) at a temperature ranging from an ice-cold temperature to room temperature.

The proportion of the bromo compound of formula (XI) to the compound of formula (II) may generally be such that the bromo compound of formula (XI) is used in an amount of at least 1 mole, preferably 1 to 2 moles, and more preferably 1 to 1.5 moles, per mole of the compound of formula (II). The strong base may generally be used in an amount of at least 1 mole, preferably 1 to 2 moles, and more preferably 1 to 1.5 moles, per mole of the compound of formula (II).

In the above-described process (h), the reaction of a compound of formula (II) with an aldehyde compound of formula (XII) may be carried out in the same manner as described above in connection with the process (a).

In the above-described process (i), the reaction of a carboxy compound of formula (VII) with 1,2,3,4-tetrahydroisoquinoline may be carried out in the same manner as described above in connection with the process (e).

In the above-described process (j), the treatment of a compound of formula (I) in which $R^2$ is a hydrogen atom, with a lower alkyl halide or an aralkyl halide may generally be carried out in an inert organic solvent selected, for example, from ethers such as dioxane, tetrahydrofuran and dimethoxyethane; amides such as dimethylformamide and dimethylacetamide; and aromatic hydrocarbons such as benzene and toluene, and with the aid of a base such as sodium hydride, sodium amide or potassium t-butoxide. The lower alkyl halides which can be used in this treatment include, for example, methyl iodide, ethyl iodide and isopropyl iodide. The aralkyl halide which can be used include, for example, benzyl iodide and phenethyl iodide. As the reaction temperature, it is usually suitable to employ a temperature ranging from about 0° C. to the reflux temperature of the reaction mixture and preferably from an ice-cold temperature to room temperature.

The proportion of the lower alkyl halide or aralkyl halide to the compound of formula (I) in which $R^2$ is a hydrogen atom may generally be such that the lower alkyl halide or aralkyl halide is used in an amount of at least 1 mole, preferably 1.05 to 2 moles, and more preferably 1.1 to 1.5 moles, per mole of the compound of formula (I).

In this reaction, when lower alkyl group represented by $R^2$ is substituted by hydroxyl or amino, it is advantageous to protect this substituent group suitably with an appropriate protecting group (e.g., cyclic imide, dibenzyl, benzyloxycarbonyl or t-butoxycarbonyl for amino; and benzyl, acetyl or methoxymethyl for hydroxyl) in advance and eliminate the protecting group after completion of the reaction.

Thus, the substituted pyrazole compounds of the above formula (I) which are desired in the present invention can be formed.

The compounds of the above formula (I) or their salts, which have been formed in the above-described manner, may be isolated and purified from the reaction mixture by per se known techniques such as recrystallization, distillation, column chromatography and thin-layer chromatography.

The compounds of the above formula (II), which are used as starting materials in the above-described reactions, are novel compounds which have not been described in the literature of the prior art. They may readily be prepared, for example, by treating a compound of the following formula (XIII) with formaldehyde and pyrrolidine.

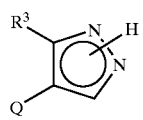

(XIII)

wherein $R^3$ and Q have the above-defined meanings. For the details of the reaction conditions, reference should be made to Synthesis Example 1 which will be given later.

The substituted pyrazole compounds of formula (I) or their salts in accordance with the present invention, which have been described above, have an excellent p38MAP kinase inhibiting effect and are hence exhibit an inhibitory effect on the production of TNF-α, IL-1, IL-6, COX-II and the like. Accordingly, they are useful as agents for the treatment of TNF-α-related diseases, IL-1-related diseases, IL-6-related diseases and COX-II-related diseases, such as rheumatoid arthritis, multiple sclerosis, osteoarthritis, psoriasis, HIV, asthma, septic shock, IBD, Crohn's disease, Alzheimer's disease, diabetes, cachexia, osteoporosis, graft versus host disease, adult RDS, arteriosclerosis, gout, glomerulonephritis, congestive heart failure, ulcerative colitis, sepsis, cerebral malaria, restenosis, hepatitis, SLE, thrombosis, born resorption disease, chronic pulmonary inflammation disease, cardiac reperfusion injury, renal reperfusion injury, cancer, Reiter's syndrome, preterm labor, eczema, allograft rejection, stroke, fever, Behcet's disease, neuralgia, meningitis, sunburn, contact dermatitis, acute synovitis, spondylitis, muscle degeneration, angiogenesis, conjunctivitis, psoriatic arthritis, viral myocarditis, pancreatitis, glioblastoma, bleeding, joint inflammation, endotoxic shock, parasitic infections, tuberculosis, myocardial infarction, leprosy, diabetic retinopathy, IBS, transplant rejection, burns, bronchitis, ischemic heart disease, eclampsia, pneumonia, remission of swelling, low back pain, laryngopharyngitis, Kawasaki disease, myelopathy and atopic dermatitis.

The p38MAP kinase inhibiting effects of the compounds of formula (I) or their salts in accordance with the present invention can be measured in the following manner.

(1) Measurement of inhibitory activities against the binding of p38MAP kinase

Inhibitory activities against the binding of p38MAP kinase were measured by use of the cytosol fraction of THP-1 cells which are cultured cells derived from human monocytes. Specifically, THP-1 cells were suspended in a cell lysis buffer [20 mM Tris-HCl buffer (pH 7.4), 1 mM magnesium chloride, 1 mM PMSF (phenylmethylsulfonyl fluoride), 1 mM pepstatin A, 1 mM leupeptin, 10 mg/ml aprotinin] and then ultrasonicated in water. Thereafter, the suspension was centrifuged at 100,000×g for 1 hour, and the protein concentration of the resulting supernatant (cytosol fraction) was determined. This supernatant was diluted with the cell lysis buffer so that the protein concentration of the cytosol fraction was 1 mg/ml, dispensed, and stored at −80° C. till use.

The inhibitory activity of a test compound against the binding of p38MAP kinase was measured by incubating a mixture of the cytosol fraction (100 μg protein) of THP-1 cells and the test compound at 15° C. for 30 minutes, adding thereto 1.11 KBq of $^3$H-SB202190 (925 GBq/mmol; manufactured by Amersham, England) as a radioligand, and reacting the resulting mixture at 15° C. for 3 hours. Nonspecific binding was measured by adding 20 μM SB203580. In order to separate the free and bound types of radioligand, a charcoal solution (1% charcoal, 0.1% dextran T-70). The resulting mixture was cooled with ice for 15 minutes and then centrifuged (3,000 rpm, 10 minutes, 4° C.). After the addition of a liquid scintillator to the resulting supernatant, its radioactivity was measured with a liquid scintillation counter.

$^3$H-SB202190 used as a radioligand was 4-(4-fluorophenyl)-2-(4-hydroxy-3,5-di-$^3$H-phenyl)-5-(4-pyridyl)imidazole, and SB203580 added for the measurement of nonspecific binding was 4-(4-fluorophenyl)-2-(4-methanesulfonylphenyl)-5-(4-pyridyl)imidazole.

The results of measurement of compounds in accordance with the present invention are given below.

| Compound | IC50 (nM) |
| --- | --- |
| Example 3 | 0.546 |
| Example 5 | 0.99 |
| Example 7 | 0.203 |
| Example 8 | 0.205 |
| Example 15 | 0.316 |
| Example 25 | 0.431 |
| Example 26 | 0.0200 |
| Example 27 | 0.000786 |
| Example 28 | 0.0579 |
| Example 30 | 0.0956 |
| Example 31 | 0.329 |
| Example 39 | 0.335 |
| Example 40 | 0.0400 |
| Example 41 | 0.00851 |
| Example 42 | 0.0170 |
| Example 43 | 0.0000115 |
| Example 47 | 0.471 |
| Example 50 | 0.402 |
| Example 54 | 0.11 |
| Example 55 | 0.226 |
| Example 57 | 0.365 |
| Example 58 | 0.284 |
| Example 61 | 0.042 |
| Example 62 | 0.114 |
| Example 73 | 0.310 |
| Example 74 | 0.302 |
| Example 75 | 0.0484 |
| Example 76 | 0.0279 |
| Example 77 | 0.335 |
| Example 82 | 0.154 |
| Example 83 | 0.175 |
| Example 86 | 0.358 |
| Example 91 | 0.231 |

As described above, the compounds of the above formula (I) or salts thereof in accordance with the present invention have an excellent inhibitory activity against the binding of p38MAP kinase, and can hence be used as p38MAP kinase inhibitors for purposes of prophylaxis, therapy and treatment in human beings and other mammals by oral administration or parenteral administration (e.g., intramuscular injection, intravenous injection, intra-articular administration, intrarectal administration or percutaneous administration).

When the compounds of the present invention are used as drugs, they may be formed into any of various pharmaceutical preparations according to the intended purpose. These pharmaceutical preparations include solid preparations (e.g., tablets, hard capsules, soft capsules, granules, powders, fine subtilaes, pills, troches and patches), semisolid preparations (e.g., suppositories and ointments), and liquid preparations (e.g., injections, emulsions, suspensions, lotions and sprays). Nontoxic additives which can be used in the aforesaid pharmaceutical preparations include, for example, starch, gelatin, glucose, lactose, fructose, maltose, magnesium carbonate, talc, magnesium stearate, methylcellulose, carboxymethylcellulose and salts thereof, acacia, polyethylene glycol, alkyl esters of p-hydroxybenzoic acid, syrup, ethanol, propylene glycol, petrolatum, carbowax, glycerin, sodium chloride, sodium sulfite, sodium phosphate and citric acid. The aforesaid pharmaceutical preparations may also contain other therapeutically useful drugs.

The content of the compounds of the present invention in the aforesaid pharmaceutical preparations may vary according to the dosage form. Generally, it is desirable that solid and semisolid preparations contain the compounds of the present invention at a concentration of 0.1 to 50% by weight and liquid preparations contain them at a concentration of 0.05 to 10% by weight.

The dosage of the compounds of the present invention may vary widely according to the type and body weight of the mammal (including human being) to be treated, the route of administration, the severity of symptoms, the doctor's diagnosis, and the like. Generally, they may be administered in a daily dose of 0.02 to 10 mg/kg and preferably 0.1 to 2 mg/kg. However, it is a matter of course that they may be administered in doses less than the lower limit of the aforesaid range or greater than the upper limit thereof, depending on the severity of symptoms in the patient and the doctor's diagnosis. The aforesaid daily dose may be given at a time or in several divided doses.

EXAMPLES

The present invention is more specifically explained with reference to the following examples and preparation example.

Preparation Example 1

(a) 3.21 mg of 3-dimethylamino-1-(4-fluorophenyl)-2-(4-pyridyl)-2-propen-1-one was dissolved in 60 ml of ethanol, and 2.9 ml of hydrazine monohydrate was added thereto, followed by heating under reflux for 2 hours. After the reaction, mixture was concentrated under reduced pressure and 80 ml of water was added thereto, the resulting mixture was extracted twice with ethyl acetate. The combined organic layer was washed with 40 ml of a saturated aqueous solution of sodium chloride. After the organic layer was dried over anhydrous magnesium sulfate, the solvent was distilled off under reduced pressure. The resulting residue was recrystallized from ethyl acetate to obtain 2.48 g (86% yield) of 3(5)-(4-fluorophenyl)-4-(4-pyridyl)pyrazole as yellow prismatic crystals.

Melting point: 208.5–209° C.; $^1$H-NMR (CDCl$_3$) δ: 8.51 (dd, J=1.5, 4.5 Hz, 2H), 7.82 (s, 1H), 7.5–6.9 (m, 6H); IR (KBr) ν max: 2840, 1606, 1518, 1222, 834, 814 cm$^{-1}$; Mass, m/e: 239 (M$^+$, base).

(b) 1.66 g of 3(5)-(4-fluorophenyl)-4-(4-pyridyl)pyrazole and 1.05 ml of a 37% formaldehyde solution were dissolved in 20 ml of ethanol, and 1.17 ml of pyrrolidine was added thereto, followed by heating under reflux for 5 hours. After the reaction, mixture was concentrated under reduced pressure and 50 ml of water was added thereto, the resulting mixture was extracted twice with 70 ml portions of ethyl acetate. The combined organic layer was washed twice with 50 ml portions of water and then with 20 ml of a saturated aqueous solution of sodium chloride. After the organic layer was dried over anhydrous sodium sulfate, the solvent was distilled off under reduced pressure. Thus, 2.17 g (97% yield) of 3-(4-fluorophenyl)-4-(4-pyridyl)-1-(1-pyrrolidinomethyl)pyrazole was obtained as a yellow solid material.

$^1$H-NMR (CDCl$_3$) δ: 8.49 (dd, J=1.6, 4.5 Hz, 2H), 7.70 (s, 1H), 7.6–7.9 (m, 6H), 5.08 (s, 2H), 2.9–2.5 (m, 4H), 2.0–1.6 (m, 4H); IR (KBr) ν max: 1602, 1222, 1142 cm$^{-1}$; Mass, m/e: 239 (M$^+$ −83), 84 (base).

Example 1

Synthesis of 3(5)-(4-Fluorophenyl)-5(3)-(1-hydroxy-3-phenylpropyl)-4-(4-pyridyl)pyrazole 3.89 g of 3-(4-fluorophenyl)-4-(4-pyridyl)-1-(1-pyrrolidinomethyl)pyrazole was dissolved in 100 ml of tetrahydrofuran. While this solution was being stirred at −70° C. or below, 8.3 ml of a 1.6M hexane solution of butyl lithium was added dropwise thereto. After the stirring was continued for 30 minutes, 15 ml of a tetrahydrofuran solution containing 1.77 g of 3-phenylpropionaldehyde was added dropwise thereto. After this mixture was gradually returned to room temperature and stirred for 1 hour, 24 ml of 1M hydrochloric acid was added thereto. After 10 minutes, the reaction mixture was alkalified with a saturated aqueous solution of sodium hydrogen carbonate and the resulting organic layer was separated. The aqueous layer was further extracted twice with 50 ml portions of ethyl acetate. The combined organic layer was washed with 30 ml of a saturated aqueous solution of sodium chloride and dried over anhydrous magnesium sulfate. After the solvent was distilled off under reduced pressure, the resulting residue was purified by silica gel column chromatography using 200 g of silica gel (with an elution solvent comprising ethyl acetate). Thus, 2.27 g (51% yield) of the title compound was obtained as a white amorphous compound.

$^1$H-NMR (CDCl$_3$) δ: 8.43 (dd, J=1.5, 4.6 Hz, 2H), 6.8–7.4 (m, 11H), 5.0–4.7 (m, 1H), 5.0–4.0 (bs, 1H), 2.69 (t, J=7.3 Hz, 2H), 2.2–1.9 (m, 2H); IR (KBr) ν max: 3160, 2880, 1602, 1518, 1220, 968, 834 cm$^{-1}$; Mass, m/e: 373 (M$^+$), 269 (base).

The compounds of the following Examples 2–17 were synthesized in substantially the same manner as in Example 1.

Example 2

3(5)-(4-Fluorophenyl)-5(3)-(1-hydroxy-2-phenylethyl)-4-(4-pyridyl)pyrazole

A white amorphous compound; $^1$H-NMR (CDCl$_3$) δ: 8.49 (dd, J=1.5, 4.4 Hz, 2H), 7.5–6.7 (m, 11H), 5.05 (t, J=6.8 Hz, 1H), 3.04 (d, J=6.8 Hz, 2H); IR (KBr) ν max: 3200, 2930, 1604, 1518, 1224, 836 cm$^{-1}$; Mass, m/e: 359 (M$^+$), 268 (base).

Example 3

3(5)-(4-Fluorophenyl)-5(3)-(1-hydroxy-4-phenylbutyl)-4-(4-pyridyl)pyrazole

A white amorphous compound; $^1$H-NMR (CDCl$_3$) δ: 8.5 (dd, J=1.5, 4.6 Hz, 2H), 7.4–6.6 (m, 11H), 5.0–4.7 (m, 1H), 2.54 (t, J=6.5 Hz, 2H), 2.0–1.4 (m, 4H); IR (KBr) ν max: 3190, 2940, 1604, 1510, 1220, 836 cm$^{-1}$; Mass, m/e: 387 (M$^+$), 91 (base).

Example 4

3(5)-(4-Fluorophenyl)-5(3)-[1-hydroxy-3-(2-tolyl)propyl]-4-(4-pyridyl)pyrazole

A pale-yellow amorphous compound; $^1$H-NMR (CDCl$_3$) δ: 8.45 (dd, J=1.5, 4.4 Hz, 2H), 7.5–6.8 (m, 11H), 5.0–4.8 (m, 1H), 2.9–2.4 (m, 2H), 2.4–1.8 (m, 5H), 2.15 (s, 3H); IR (KBr) ν max: 3190, 2926, 1606, 1520, 1446, 1224, 1066, 836 cm$^{-1}$; Mass, m/e: 369 (M$^+$ −2), 269 (base).

Example 5

3(5)-(4-Fluorophenyl)-5(3)-[1-hydroxy-3-(3-tolyl)propyl]-4-(4-pyridyl)pyrazole

A pale-yellow amorphous compound; $^1$H-NMR (CDCl$_3$) δ: 8.45 (dd, J=1.6, 4.5 Hz, 2H), 7.5–6.7 (m, 11H), 5.0–4.7 (m, 1H), 2.66 (t, J=7.3 Hz, 2H), 2.27 (s, 3H), 2.2–1.8 (m, 2H); IR (KBr) ν max: 3200, 2920, 1604, 1222, 838 cm$^{-1}$; Mass, m/e: 369 (M$^+$ −2), 269 (base).

Example 6

5(3)-[3-(2-Chlorophenyl)-1-hydroxypropyl]-3(5)-(4-fluorophenyl)-4-(4-pyridyl)pyrazole A white amorphous compound; $^1$H-NMR (CDCl$_3$) δ: 8.47 (dd, J=4.4, 1.5 Hz, 2H), 7.40–6.88 (m, 10H), 4.89 (t, J=6.4 Hz, 1H), 2.85 (m, 2H), 2.11 (m, 2H); IR (KBr) ν max: 3600–2700, 1606, 1512 cm$^{-1}$; Mass, m/e: 407 (M$^+$), 269 (base).

Example 7

3(5)-(4-Fluorophenyl)-5(3)-(1-hydroxy-3-phenylbutyl)-4-(4-pyridyl)pyrazole

A white amorphous compound; $^1$H-NMR (CDCl$_3$) δ: 8.5 (dd, J=1.5, 4.6 Hz, 2H), 7.4–6.6 (m, 11H), 5.0–4.7 (m, 1H), 2.54 (t, J=6.5 Hz, 2H), 2.0–1.4 (m, 4H); IR (KBr) ν max: 3190, 2940, 1604, 1510, 1220, 836 cm$^{-1}$; Mass, m/e: 387 (M$^+$), 91 (base).

Example 8

3(5)-(4-Fluorophenyl)-5(3)-(1-hydroxy-2-methyl-3-phenylpropyl)-4-(4-pyridyl)pyrazole (a Mixture of Diastereomers)

A white amorphous compound; $^1$H-NMR (CDCl$_3$) δ: 8.55 (dd, J=1.6, 4.5 Hz, 1H), 8.44 (dd, J=1.5, 4.5 Hz, 1H), 7.4–6.8 (m, 11H), 4.9–4.7 (m, 1H), 3.0–2.0 (m, 3H), 0.86 (d, J=6.6 Hz, 1.5H), 0.74 (d, J=6.4 Hz, 1.5H); IR (KBr) ν max: 3180, 2960, 1606, 1518, 1222, 838 cm$^{-1}$; Mass, m/e: 387 (M$^+$), 268 (base).

Example 9

3(5)-(4-Fluorophenyl)-5(3)-(1-hydroxy-3-pentafluorophenylpropyl)-4-(4-pyridyl)pyrazole $^1$H-NMR (CDCl$_3$) δ: 8.55 (dd, J=1.5, 4.4 Hz, 2H), 7.4–6.9 (m, 6H), 4.89 (t, J=6.2 Hz, 1H), 2.95–2.65 (m, 2H), 2.2–1.85

(m, 2H); IR (KBr) ν max: 1608, 1518, 1503, 966, 837 cm$^{-1}$; Mass, m/e: 463 (M$^+$), 269 (base).

Example 10

3(5)-(4-Fluorophenyl)-5(3)-[1-hydroxy-3-(2-pyridyl)propyl]-4-(4-pyridyl)pyrazole A white amorphous compound; $^1$H-NMR (CDCl$_3$) δ: 8.53 (dd, J=1.7, 4.4 Hz, 2H), 8.5–8.4 (m, 1H), 7.8–6.8 (m, 9H), 5.2–5.0 (m, 1H), 3.1–2.8 (m, 2H), 2.3–1.9 (m, 2H); IR (KBr) ν max: 3180, 2930, 1604, 1516, 1438, 1222, 838 cm$^{-1}$; Mass, m/e: 374 (M$^+$), 93 (base).

Example 11

(5)-(4-Fluorophenyl)-5(3)-[1-hydroxy-3-(3-pyridyl)propyl]-4-(4-pyridyl)pyrazole

A pale-yellow amorphous compound; $^1$H-NMR (CDCl$_3$) δ: 8.47 (dd, J=1.5, 4.4 Hz, 2H), 8.4–8.2 (m, 2H), 7.5–6.8 (m, 8H), 4.9–4.7 (m, 1H), 2.8–2.6 (m, 2H), 2.2–1.9 (m, 2H); IR (KBr) ν max: 3120, 2940, 1604, 1520, 1422, 1222, 838 cm$^{-1}$; Mass, m/e: 374 (M$^+$), 269 (base).

Example 12

3(5)-(4-Fluorophenyl)-5(3)-[1-hydroxy-2-methyl-3-(3-pyridyl)propyl]-4-(4-pyridyl)pyrazole (a Mixture of Diastereomers)

A pale-yellow amorphous compound; $^1$H-NMR (CDCl$_3$) δ: 8.53 (dd, J=1.6, 4.5 Hz, 1H), 8.43 (dd, J=1.6, 4.5 Hz, 1H), 8.4–8.2 (m, 2H), 7.4–6.88 (m, 8H), 4.8–4.6 (m, 1H), 3.1–1.9 (m, 3H), 0.89 (d, J=6.6 Hz, 1.5H), 0.72 (d, J=6.4 Hz, 1.5H); IR (KBr) ν max: 3170, 2960, 1604, 1516, 1424, 1222, 838 cm$^{-1}$; Mass, m/e: 388 (M$^+$), 106 (base).

Example 13

3(5)-(4-Fluorophenyl)-5(3)-[1-hydroxy-3-(3-pyridyl)butyl]-4-(4-pyridyl)pyrazole (a Mixture of Diastereomers)

A white amorphous compound; $^1$H-NMR (CDCl$_3$) δ: 8.6–8.3 (m, 3H), 7.8–6.8 (m, 9H), 5.2–4.9 (m, 1H), 3.4–3.0 (m, 1H), 2.5–1.7 (m, 2H), 1.4–1.1 (m, 3H); IR (KBr) ν max: 3200, 2960, 1606, 1520, 1436, 1224, 838 cm$^{-1}$; Mass, m/e: 388 (M$^+$), 107 (base).

Example 14

3(5)-(4-Fluorophenyl)-5(3)-[1-hydroxy-3-(5-pyrimidinyl)propyl]-4-(4-pyridyl)pyrazole A colorless waxy compound; $^1$H-NMR (CDCl$_3$) δ: 8.99 (s, 1H), 8.52 (dd, J=1.5, 4.6 Hz, 2H), 8.45 (s, 2H), 7.33–6.89 (m, 4H), 7.09 (dd, J=1.5, 4.6 Hz, 2H), 5.00–4.70 (m, 1H), 2.80–2.60 (m, 2H), 2.20–1.97 (m, 2H); IR (KBr) ν max: 3332, 1604, 1412, 1220, 836 cm$^{-1}$; Mass, m/e: 375 (M$^+$), 269 (base).

Example 15

3-(4-Fluorophenyl)-5-(1-hydroxy-3-phenylpropyl)-1-methyl-4-(4-pyridyl)pyrazole

A pale-yellow solid material; Melting point: 62–65° C.; $^1$H-NMR (CDCl$_3$) δ: 8.39 (dd, J=1.5, 4.4 Hz, 2H), 7.4–6.7 (m, 11H), 4.9–4.6 (m, 1H), 4.07 (s, 3H), 2.9–1.9 (m, 4H); IR (KBr) ν max: 3210, 2940, 1604, 1524, 1446, 1222, 840 cm$^{-1}$; Mass, m/e: 387 (M$^+$), 282 (base).

Example 16

3-(4-Fluorophenyl)-5-[1-hydroxy-3-(3-pyridyl)propyl]-1-methyl-4-(4-pyridyl)pyrazole A colorless oily material; $^1$H-NMR (CDCl$_3$) δ: 8.63–8.29 (m, 4H), 7.47–6.75 (m, 8H), 3.85 (s, 3H), 2.83–2.46 (m, 4H), 2.06–1.53 (m, 2H); IR (KBr) ν max: 2932, 1600, 1522, 1480, 1446, 1422, 1220, 1156, 838 cm$^{-1}$; Mass, m/e: 372 (M$^+$), 266 (base).

Example 17

5(3)-(3-Cyclohexyl-1-hydroxypropyl)-3(5)-(4-fluorophenyl)-4-(4-pyridyl)pyrazole

Melting point: 86.7–88.2° C.; $^1$H-NMR (CDCl$_3$) δ: 8.52 (dd, J=1.5, 4.6 Hz, 2H), 7.11 (dd, J=1.5, 4.6 Hz, 2H), 7.14–6.86 (m, 4H), 4.83 (t, J=6.4 Hz, 1H), 1.89–0.61 (m, 15H); IR (KBr) ν max: 3600–2800, 2924, 1604, 1516 cm$^{-1}$; Mass, m/e: 379 (M$^+$).

Example 18

Synthesis of 3(5)-(4-Fluorophenyl)-5(3)-(3-phenyl-1-propenyl)-4-(4-pyridyl)pyrazole 10 ml of toluene was added to 373 mg of 3(5)-(4-fluorophenyl)-5(3)-(1-hydroxy-3-phenylpropyl)-4-(4-pyridyl)pyrazole and 399 mg of 4-toluenesulfonic acid monohydrate, followed by heating under reflux for 24 hours. The reaction mixture was alkalified with a saturated aqueous solution of sodium hydrogen carbonate and then extracted three times with 30 ml portions of a solvent mixture comprising chloroform-methanol (9:1). After the combined organic layer was washed twice with 10 ml portions of a saturated aqueous solution of sodium chloride and dried over anhydrous magnesium sulfate, the solvent was distilled off under reduced pressure. The resulting residue was subjected to silica gel column chromatography using 40 g of silica gel (with an elution solvent comprising chloroform), and then recrystallized from ethyl acetate. Thus, 160 mg (45% yield) of the title compound was obtained as a white powder.

Melting point: 204–205.5° C.; $^1$H-NMR (CDCl$_3$) δ: 8.55 (dd, J=1.6, 4.5 Hz, 2H), 7.5–6.7 (m, 11H), 6.4–6.1 (m, 2H), 3.52 (d, J=5.1 Hz, 2H); IR (KBr) ν max: 3220, 1600, 1516, 1442, 1220, 974, 838, 828 cm$^{-1}$; Mass, m/e: 355 (M$^+$, base)

The compounds of the following Examples 19–30 were synthesized in substantially the same manner as in Example 18.

Example 19

3(5)-(4-Fluorophenyl)-5(3)-(2-phenyl-1-ethenyl)-4-(4-pyridyl)pyrazole

A white powder; Melting point: 231–233° C.; $^1$H-NMR (CDCl$_3$) δ: 8.53 (dd, J=1.5, 4.5 Hz, 2H), 7.6–6.7 (m, 13H); IR (KBr) ν max: 3100, 1600, 1516, 1220, 838, 828 cm$^{-1}$; Mass, m/e: 340 (M$^+$ −1, base).

Example 20

3(5)-(4-Fluorophenyl)-5(3)-(4-phenyl-1-butenyl)-4-(4-pyridyl)pyrazole

A white amorphous compound; $^1$H-NMR (CDCl$_3$) δ: 8.53 (dd, J=1.5, 4.5 Hz, 2H), 7.5–6.8 (m, 11H), 6.3–6.0 (m, 2H), 2.9–2.3 (m, 4H); IR (KBr) ν max: 2930, 1602, 1520, 1222, 836 cm$^{-1}$; Mass, m/e: 369 (M$^+$), 278 (base).

Example 21

3(5)-(4-Fluorophenyl)-4-(4-pyridyl)-5(3)-[3-(2-tolyl)-1-propenyl]pyrazole

A white powder; Melting point: 203.5–206° C.; $^1$H-NMR (CDCl$_3$) δ: 10.6–10.2 (bs, 1H), 8.54 (dd, J=1.8, 4.4 Hz, 2H), 7.5–6.8 (m, 10H), 6.4–6.1 (m, 2H), 3.51 (d, J=4.8 Hz, 2H), 2.29 (s, 3H); IR (KBr) ν max: 2930, 1602, 1520, 1444, 1216, 836 cm$^{-1}$; Mass, m/e: 369 (M$^+$), 252 (base).

Example 22

3(5)-(4-Fluorophenyl)-4-(4-pyridyl)-5(3)-[3-(3-tolyl)-1-propenyl]pyrazole

A white powder; Melting point: 191.5–200.5° C.; $^1$H-NMR (CDCl$_3$) δ: 10.6–10.2 (bs, 1H), 8.56 (dd, J=1.8, 4.4 Hz, 2H), 7.5–6.8 (m, 10H), 6.4–6.1 (m, 2H), 3.6–3.3 (m, 2H), 2.33 (s, 3H); IR (KBr) ν max: 2920, 1602, 1518, 1220, 832 cm$^{-1}$; Mass, m/e: 369 (M$^+$, base).

Example 23

5(3)-[3-(2-Chlorophenyl)-1-propenyl]-3(5)-(4-fluorophenyl)-4-(4-pyridyl)pyrazole A white powder; Melting point: 192.4–193.43° C.; $^1$H-NMR (CDCl$_3$) δ: 8.55 (dd, J=4.4, 1. 5 Hz, 2H), 7.41–6.92 (m, 10H), 6.30 (m, 2H), 3.64 (b, J=4.8 Hz, 2H); IR (KBr) ν max: 1604, 1518 cm$^{-1}$; Mass, m/e: 389 (M$^+$), 51 (base).

Example 24

3(5)-(4-Fluorophenyl)-5(3)-(3-phenyl-1-butenyl)-4-(4-pyridyl)pyrazole

A white powder; Melting point: 142.2–143.0° C.; $^1$H-NMR (CDCl$_3$) δ: 8.48 (dd, J=1.5, 4.5 Hz, 2H), 7.4–6.8 (m, 11H), 6.50 (dd, J=5.9, 16.26 Hz, 1H), 6.18 (d, J=16. 26 Hz, 1H), 3.7–3.3 (m, 1H), 1.44 (d, J=6.94 Hz, 3H); IR (KBr) ν max: 3152, 3100, 3060, 3024, 2964, 2924, 1602, 1506, 1224, 1506, 834 cm$^{-1}$; Mass, m/e: 369 (M$^+$, Base), 354 (M$^+$ −CH$_3$), 115

Example 25

3(5)-(4-Fluorophenyl)-4-(4-pyridyl)-5(3)-[3-(2-pyridyl)-1-propenyl]pyrazole (a Mixture of E- and Z-isomers)

A white amorphous compound; $^1$H-NMR (CDCl$_3$) δ: 8.6–8.4 (m, 3H), 7.7–6.4 (m, 9H), 3.8–3.5 (m, 2H); IR (KBr) ν max: 2950, 1604, 1514, 1434, 1222, 836 cm$^{-1}$; Mass, m/e: 356 (M$^+$), 355 (base).

Example 26

3(5)-(4-Fluorophenyl)-4-(4-pyridyl)-5(3)-[3-(3-pyridyl)-1-propenyl]pyrazole

White flaky crystals; Melting point: 187–188° C.; $^1$H-NMR (CDCl$_3$) δ: 8.54 (dd, J=1.6, 4.5 Hz, 2H), 8.5–8.3 (m, 2H), 7.6–6.8 (m, 8H), 6.5–6.3 (m, 2H), 3.53 (d, J=4.8, 2H); IR (KBr) ν max: 2800, 1600, 1422, 1216, 970, 834 cm$^{-1}$; Mass, m/e: 356 (M$^+$, base).

Example 27

3(5)-(4-Fluorophenyl)-5(3)-[2-methyl-3-(3-pyridyl)-1-propenyl]-4-(4-pyridyl)pyrazole A white powder; Melting point: 215.5–217.5° C.; $^1$H-NMR (CDCl$_3$) δ: 8.6–8.4 (m, 4H), 7.6–6.9 (m, 9H), 6.08 (d, J=1.3 Hz, 1H), 3.46 (s, 2H), 1.83 (d, J=1.3 Hz, 3H); IR (KBr) ν max: 2780, 1606, 1510, 1220, 834 cm$^{-1}$; Mass, m/e: 370 (M$^+$, base).

Example 28

3(5)-(4-Fluorophenyl)-4-(4-pyridyl)-5(3)-[3-(2-pyridyl)-1-butenyl]pyrazole

A white amorphous compound; $^1$H-NMR (CDCl$_3$) δ: 8.6–8.5 (m, 3H), 7.8–6.3 (m, 11H) 3.9–3.5 (m, 2H), 2.13 (d, J=7.0 Hz, 3H); IR (KBr) ν max: 1604, 1516, 1222, 1436, 836 cm$^{-1}$; Mass, m/e: 370 (M$^+$, base).

Example 29

3-(4-Fluorophenyl)-1-methyl-5-(3-phenyl-1-propenyl)-4-(4-pyridyl)pyrazole

A white powder; Melting point: 136–137° C.; $^1$H-NMR (CDCl$_3$) δ: 8.49 (dd, J=1.8, 4.4 Hz, 2H), 7.5–6.8 (m, 11H), 6.4–5.7 (m, 2H), 3.93 (s, 3H), 3.49 (d, J=5.7 Hz, 2H); IR (KBr) ν max: 1598, 1522, 1444, 1218, 974, 844 cm$^{-1}$; Mass, m/e: 369 (M$^+$), 278 (base).

Example 30

3-(4-Fluorophenyl)-1-methyl-4-(4-pyridyl)-5-[3-(3-pyridyl)-1-propenyl]pyrazole $^1$H-NMR (CDCl$_3$) δ: 8.63–8.29 (m, 4H), 7.5–6.8 (m, 8H), 6.4–5.7 (m, 2H), 3.93 (s, 3H), 3.49 (d, J=6.38 Hz, 2H); IR (KBr) ν max: 1602, 1524, 1479, 1218, 843 cm$^{-1}$; Mass, m/e: 370 (M$^+$), 278 (base).

Example 31

Synthesis of 3(5)-(4-Fluorophenyl)-5(3)-(3-phenylpropyl)-4-(4-pyridyl)pyrazole 100 mg of 3(5)-(4-fluorophenyl)-5(3)-(3-phenyl-1-propenyl)-4-(4-pyridyl)pyrazole was dissolved in 30 ml of ethanol. Then, 50 mg of 5% palladium-carbon was added thereto, followed by stirring at atmospheric pressure and room temperature for 15 hours under an atmosphere of hydrogen. After the reaction, the mixture was filtered through celite, the solvent was distilled off under reduced pressure. After ether was added to the residue, the resulting crystals were separated by filtration. Thus, 60 mg (60% yield) of the title compound was obtained as a white powder.

Melting point: 155.5–156.5° C.; $^1$H-NMR (CDCl$_3$) δ: 8.52 (dd, J=1.5, 4.4 Hz, 2H), 7.4–6.8 (m, 11H), 2.9–2.5 (m, 4H), 2.2–1.7 (m, 2H); IR (KBr) ν max: 2920, 1602, 1510, 1226, 830 cm$^{-1}$; Mass, m/e: 357 (M$^+$), 252 (base).

The compounds of the following Examples 32–48 were synthesized in substantially the same manner as in Example 31.

Example 32

3(5)-(4-Fluorophenyl)-5(3)-(2-phenylethyl)-4-(4-pyridyl)pyrazole

A white powder; Melting point: 187.5–188.5° C.; $^1$H-NMR (CDCl$_3$) δ: 8.53 (dd, J=1.5, 4.4 Hz, 2H), 7.5–6.8 (m, 11H), 2.95 (s, 4H); IR (KBr) ν max: 3030, 2860, 1604, 1506, 1220, 834 cm$^{-1}$; Mass, m/e: 343 (M$^+$), 91 (base).

Example 33

3(5)-(4-Fluorophenyl)-5(3)-(4-phenylbutyl)-4-(4-pyridyl)pyrazole

A white powder; Melting point: 157–158° C.; $^1$H-NMR (CDCl$_3$) δ: 8.54 (dd, J=1.7, 4.4 Hz, 2H), 7.5–6.8 (m, 11H), 2.9–2.4 (m, 4H), 1.9–1.5 (m, 4H); IR (KBr) ν max: 2940, 1606, 1516, 1442, 1220, 836 cm$^{-1}$; Mass, m/e: 371 (M$^+$), 91 (base).

Example 34

3(5)-(4-Fluorophenyl)-4-(4-pyridyl)-5(3)-[3-(2-tolyl)propyl]pyrazole

A white powder; Melting point: 168.5–170.5° C.; $^1$H-NMR (CDCl$_3$) δ: 8.52 (dd, J=1.8, 4.4 Hz, 2H), 7.5–6.8 (m, 10H), 2.9–2.4 (m, 4H), 2.21 (s, 3H), 2.2–1.6 (m, 2H); IR (KBr) ν max: 2950, 1596, 1510, 1226, 834 cm$^{-1}$; Mass, m/e: 371 (M$^+$), 252 (base).

Example 35

3(5)-(4-Fluorophenyl)-4-(4-pyridyl)-5(3)-[3-(3-tolyl)propyl]pyrazole

A white powder; Melting point: 172.5–174° C.; $^1$H-NMR (CDCl$_3$) δ: 10.5–9.9 (bs, 1H), 8.52 (dd, J=1.5, 4.4 Hz, 2H), 7.5–6.7 (m, 10H), 2.9–2.4 (m, 4H), 2.30 (s, 3H), 2.2–1.6 (m, 2H); IR (KBr) ν max: 2920, 1602, 1508, 1224, 830 cm$^{-1}$; Mass, m/e: 371 (M$^+$), 252 (base).

Example 36

5(3)-[3-(2-Chlorophenyl)propyl]-3(5)-(4-fluorophenyl)-4-(4-pyridyl)pyrazole

A white powder; Melting point: 168.6–169.4° C.; $^1$H-NMR (CDCl$_3$) δ: 8.53 (dd, J=4.4, 1.5 Hz, 2H), 7.40–6.88 (m, 10H), 2.75 (m, 4H), 1.97 (m, 2H); IR (KBr) ν max: 1600, 1508 cm$^{-1}$; Mass, m/e: 391 (M$^+$), 252 (base).

Example 37

3(5)-(4-Fluorophenyl)-5(3)-(3-phenylbutyl)-4-(4-pyridyl)pyrazole

A white powder; Melting point: 142.0–142.5° C.; $^1$H-NMR (CDCl$_3$) δ: 8.48 (dd, J=1.5, 4.6 Hz, 2H), 7.4–6.8 (m, 11H), 2.8–2.4 (m, 3H), 2.1–1.7 (m, 2H), 1.21 (d, J=6.82 Hz, 3H); IR (KBr) ν max: 2920, 1604, 1221, 832 cm$^{-1}$; Mass, m/e: 371 (M$^+$), 253 (Base), 105.

Example 38

3(5)-(4-Fluorophenyl)-5(3)-(2-methyl-3-phenylpropyl)-4-(4-pyridyl)pyrazole

A white amorphous compound; $^1$H-NMR (CDCl$_3$) δ: 8.50 (m, 2H), 7.4–6.8 (m, 11H), 3.0–1.8 (m, 5H), 0.85 (d, J=6.4 Hz, 3H); IR (KBr) ν max: 2920, 1604, 1510, 1224, 840 cm$^{-1}$; Mass, m/e: 371 (M$^+$), 91 (base).

Example 39

3(5)-(4-Fluorophenyl)-4-(4-pyridyl)-5(3)-[3-(3-pyridyl)butyl]pyrazole

A white amorphous compound; $^1$H-NMR (CDCl$_3$) δ: 8.6–8.3 (m, 4H), 7.5–6.8 (m, 8H), 2.9–2.5 (m, 3H), 2.2–1.7 (m, 2H), 1.21 (d, J=6.8 Hz, 3H); IR (KBr) ν max: 2930, 1604, 1516, 1426, 1222, 836 cm$^{-1}$; Mass, m/e: 372 (M$^+$), 106 (base).

Example 40

3(5)-(4-Fluorophenyl)-4-(4-pyridyl)-5(3)-[3-(2-pyridyl)propyl]pyrazole

A white solid material; Melting point: 143–144.5° C.; $^1$H-NMR (CDCl$_3$) δ: 8.7–8.5 (m, 3H), 7.8–6.8 (m, 9H), 3.44 (t, J=6.7 Hz, 2H), 2.63 (t, J=6.8 Hz, 2H), 2.3–1.8 (m, 2H); IR (KBr) ν max: 2990, 1604, 1516, 1436, 1216, 836 cm$^{-1}$; Mass, m/e: 358 (M$^+$), 93 (base).

Example 41

3(5)-(4-Fluorophenyl)-5(3)-[2-methyl-3-(3-pyridyl)propyl]-4-(4-pyridyl)pyrazole

A white amorphous compound; $^1$H-NMR (CDCl$_3$) δ: 8.54 (dd, J=1.5, 4.4 Hz, 2H), 8.53–8.3 (m, 2H), 7.5–6.8 (m, 8H), 3.0–1.8 (m, 5H), 0.89 (d, J=6.4 Hz, 3H); IR (KBr) ν max: 2930, 1604, 1516, 1224, 838 cm$^{-1}$; Mass, m/e: 372 (M$^+$), 329 (base).

Example 42

3(5)-(4-Fluorophenyl)-4-(4-pyridyl)-5(3)-[3-(2-pyridyl)butyl]pyrazole

A white amorphous compound; $^1$H-NMR (CDCl$_3$) δ: 8.6–8.5 (m, 1H), 8.46 (dd, J=1.5, 4.6 Hz, 2H), 7.8–6.8 (m, 9H), 3.2–1.8 (m, 5H), 1.30 (d, J=6.8 Hz, 3H); IR (KBr) ν max: 2930, 1604, 1516, 1436, 1222, 838 cm$^{-1}$; Mass, m/e: 372 (M$^+$), 107 (base).

Example 43

3(5)-(4-Fluorophenyl)-4-(4-pyridyl)-5(3)-[3-(3-pyridyl)propyl]pyrazole

A white powder; Melting point: 207–210° C.; $^1$H-NMR (CDCl$_3$) δ: 8.51 (dd, J=1.8, 4.4 Hz, 2H), 8.5–8.3 (m, 2H), 7.5–6.7 (m, 8H), 2.9–2.2 (m, 4H), 2.2–1.7 (m, 2H); IR (KBr) ν max: 2860, 1600, 1518, 1414, 1214, 828 cm$^{-1}$; Mass, m/e: 358 (M$^+$), 252 (base).

Example 44

3(5)-(4-Fluorophenyl)-4-(4-pyridyl)-5(3)-[3-(4-pyridyl)propyl]pyrazole

A white powder; Melting point: 148.2–150.4° C.; $^1$H-NMR (CDCl$_3$) δ: 8.55 (dd, J=4.4, 1.5 Hz, 2H), 8.45 (dd, J=4.4, 1.5 Hz, 2H), 7.40–6.90 (m, 8H), 2.90–2.45 (4H, m), 2.20–1.80 (m, 2H); IR (KBr) ν max: 2924, 2852, 1602, 1516, 1218, 834 cm$^{-1}$; Mass, m/e: 358 (M$^+$), 252 (base).

Example 45

3(5)-(4-Fluorophenyl)-4-(4-pyridyl)-5(3)-[3-(5-pyrimidinyl)propyl]pyrazole

A white powder; Melting point: 242.9–247.6° C.; $^1$H-NMR (DMSO-d$_6$) δ: 12.99 (bs, 1H), 8.99 (s, 1H), 8.59 (s, 2H), 8.48 (dd, J=1.5, 4.4 Hz, 2H), 7.31–7.05 (m, 4H), 7.11 (dd, J=1.3, 4.8 Hz, 2H), 3.30–2.80 (m, 2H), 2.75–2.30 (m, 2H), 2.25–1.77 (m, 2H); IR (KBr) ν max: 1600, 1408, 1212, 832 cm$^{-1}$; Mass, m/e: 359 (M$^+$), 252 (base).

Example 46

3-(4-Fluorophenyl)-1-methyl-4-(4-pyridyl)-5-[3-(3-pyridyl)propyl]pyrazole

A colorless oily material; $^1$H-NMR (CDCl$_3$) δ: 8.63–8.29 (m, 4H), 7.47–6.75 (m, 8H), 3.85 (s, 3H), 2.83–2.46 (m, 4H), 2.06–1.53 (m, 2H); IR (KBr) ν max: 2932, 1600, 1522, 1480, 1446, 1422, 1220, 1156, 838 cm$^{-1}$; Mass, m/e: 372 (M$^+$), 266 (base).

Example 47

5(3)-(3-Phenylpropyl)-3(5)-(2-pyridyl)-4-(4-pyridyl)pyrazole $^1$H-NMR (CDCl$_3$) δ: 8.64 (dd, J=1.5, 4.4 Hz, 2H), 7.6–7.4 (m, 1H), 7.3–6.9 (m, 11H), 2.8–2.5 (m, 4H), 2.1–1.7 (m, 2H); IR (KBr) ν max: 1605, 1497, 1416, 993, 828, 789, 741 cm$^{-1}$; Mass, m/e: 340 (M$^+$), 236 (base).

Example 48

5(3)-(3-Phenylpropyl)-3(5)-(3-pyridyl)-4-(4-pyridyl)pyrazole $^1$H-NMR (CDCl$_3$) δ: 8.54 (dd, J=1.5, 4.6 Hz, 2H), 7.8–7.3 (m, 2H), 7.3–6.8 (m, 9H), 2.9–2.5 (m, 4H), 2.1–1.7 (m, 2H); IR (KBr) ν max: 1602, 1410, 699 cm$^{-1}$; Mass, m/e: 340 (M$^+$), 235 (base).

Example 49

Synthesis of 3(5)-(4-Fluorophenyl)-5(3)-[3-(2-nitrophenyl)propyl]-4-(4-pyridyl)pyrazole 192 mg of sodium t-butoxide was suspended in 5 ml of tetrahydrofuran. A solution containing 215 mg of 1-(4-fluorophenyl)-2-(4-pyridyl)ethanone in 5 ml of tetrahydrofuran was added thereto over a period of 30 seconds, followed by stirring. After yellow insoluble matter was precipitated, the stirring was continued for an additional 4 hours. Then, a solution containing 613 mg of 4-(2-nitrophenyl)butyric succinimide in 5 ml of tetrahydrofuran was slowly added dropwise thereto over a period of 10 minutes, followed by stirring at room temperature for 5 minutes. After the addition of 2 ml of water, the pH of the mixture was adjusted to 5–6 with acetic acid. Then, 0.2 ml of hydrazine monohydrate was added thereto, followed by stirring for 1 hour. After the addition of a saturated aqueous solution of sodium hydrogen carbonate, the resulting mixture was extracted with ethyl acetate. The organic layer was washed with a saturated aqueous solution of sodium chloride, dried over anhydrous magnesium sulfate, and then concentrated. The resulting residue was purified by silica gel column chromatography using 40 g of silica gel [with an elution solvent comprising chloroform-methanol (100:1)]. Thus, 160 mg (40% yield) of the title compound was obtained as a white amorphous substance.

A white amorphous compound; $^1$H-NMR (CDCl$_3$) δ: 8.54 (d, J=5.7 Hz, 2H), 8.14–7.82 (m, 2H), 7.48–6.96 (m, 6H), 7.09 (dd, J=1.5, 4.6 Hz, 2H), 2.98–2.64 (br m, 4H), 2.15–1.96 (m, 2H); IR (KBr) ν max: 3200–2500, 1600, 1518, 1346 cm$^{-1}$; Mass, m/e: 402 (M$^+$), 252 (base).

The compounds of the following Examples 50–52 were synthesized in substantially the same manner as in Example 49.

Example 50

3(5)-(4-Fluorophenyl)-5(3)-[3-(4-nitrophenyl)propyl)-4-(4-pyridyl)pyrazole $^1$H-NMR (CDCl$_3$) δ: 8.54 (dd, J=1.5, 4.6 Hz, 2H), 8.10 (d, J=8.8 Hz, 2H), 7.37–6.90 (m, 6H), 7.08 (dd, J=1.5, 4.4 Hz, 2H), 2.84–2.64 (m, 4H), 2.13–1.96 (m, 2H); IR (KBr) ν max: 3200–2500, 1604, 1506, 1338 cm$^{-1}$; Mass, m/e: 402 (M$^+$), 252 (base).

Example 51

3(5)-(3,4-Methylenedioxyphenyl)-5(3)-(3-phenylbutyl)-4-(4-pyridyl)pyrazole

Melting point: 182.4–183.1° C. (ethyl acetate); $^1$H-NMR (CDCl$_3$) δ: 8.52 (dd, J=1.8, 4.4 Hz, 2H), 7.43–7.00 (m, 8H), 6.78 (dd, J=1.9, 2.2 Hz, 2H), 5.95 (s, 2H), 2.85–2.46 (m, 4H), 2.13–1.73 (m, 2H); IR (KBr) ν max: 2856, 1598, 1494, 1454, 1232 cm$^{-1}$; Mass, m/e: 383 (M$^+$), 91 (base).

Example 52

3(5)-(4-Fluorophenyl)-5(3)-(3-phenylpropyl)-4-(4-quinolyl)pyrazole

A white amorphous compound; $^1$H-NMR (CDCl$_3$) δ: 8.89 (d, J=4.4 Hz, 1H), 8.25–8.0 (m, 1H), 7.83–6.65 (m, 13H), 5.8 (bs, 1H), 2.68–2.27 (m, 4H), 2.10–1.55 (m, 2H); IR (KBr) ν max: 1510, 1224, 838, 696 cm$^{-1}$; Mass, m/e: 407 (M$^+$), 302 (base).

Example 53

Synthesis of 5(3)-[3-(2-aminophenyl)propyl]-3(5)-(4-fluorophenyl)-4-(4-pyridyl)pyrazole 45 mg of 5(3)-[3-(2-nitrophenyl)propyl]-3(5)-(4-fluorophenyl)-4-(4-pyridyl)pyrazole was dissolved in 6 ml of methanol. Then, 2 ml of cyclohexene was added thereto, followed by the addition of 45 mg of palladium-carbon (10%). This mixture was heated under reflux for 2 hours and them filtered. The filtrate was concentrated to obtain 42 mg of the title compound quantitatively as a white amorphous substance.

$^1$H-NMR (CD$_3$OD) δ: 8.41 (d, J=4.0 Hz, 2H), 7.41–6.81 (m, 10H), 2.78 (m, 4H), 1.91 (m, 2H); IR (KBr) ν max: 3500–2900, 1602, 1508 cm$^{-1}$; Mass, m/e: 372 (M$^+$), 252 (base).

The compound of the following Example 54 was synthesized in substantially the same manner as in Example 53.

Example 54

5(3)-[3-(4-Aminophenyl)propyl]-3(5)-(4-fluorophenyl)-4-(4-pyridyl)pyrazole $^1$H-NMR (CD$_3$OD) δ: 8.42 (br m, 2H), 7.41–6.62 (m, 10H), 2.72 (m, 2H), 2.49 (t, J=7.3 Hz, 2H), 1.84 (t, J=7.3 Hz, 2H); IR (KBr) ν max: 3500–2800, 1602, 1512 cm$^{-1}$; Mass, m/e: 372 (M$^+$), 252 (base).

Example 55

(a) Synthesis of 4-Benzyloxybutanol

While a suspension containing 2.5 g of 60% sodium hydride was in 50 ml of tetrahydrofuran was allowed to stand at room temperature, 5.7 g of 1,4-butanediol was slowly added dropwise thereto. Then, a solution containing 7.5 ml of benzyl bromide in 20 ml of tetrahydrofuran was added dropwise to the reaction mixture at room temperature, followed by stirring at the same temperature for 2 hours. After the addition of a 10% aqueous solution of HCl, the reaction mixture was extracted with diethyl ether. After the organic layer was washed with an aqueous solution of sodium hydrogen carbonate and dried over anhydrous magnesium sulfate, the solvent was distilled off under reduced pressure. The resulting residue was purified by silica gel column chromatography using 150 g of silica gel [with an elution solvent comprising hexane-ethyl acetate (4:1)]. Thus, 5.5 g (48% yield) of the title compound was obtained.

$^1$H-NMR (CDCl$_3$) δ: 7.32 (s, 5H), 4.51 (s, 2H), 3.58 (m, 4H), 1.69 (m, 4H); Mass, m/e: 180 (M$^+$), 91 (base).

(b) Synthesis of 4-Benzyloxybutyric Acid 3.0 g of 4-benyloxybutanol and 182 mg of TEMPO (2,2,6,6-tetramethyl-1-piperidinyloxy, radical) were dissolved in a mixture composed of 60 ml of acetonitrile and 60 ml of phosphate buffer (pH 6.7). To this reaction mixture were added 20 ml of an aqueous solution of sodium chlorite ($NaClO_2$) (3.8 g) and 0.5 ml of a 5% aqueous solution of sodium hypochlorite (NaClO), followed by stirring at 35° C. for 5.5 hours. The reaction mixture was adjusted to pH 8.0 by the addition of a 2M aqueous solution of sodium hydroxide, and stirred for 20 minutes. Thereafter, 84 ml of an aqueous solution of sodium sulfate (5.1 g) was added thereto under cooling with ice so that its internal temperature would not exceed 20° C., followed by stirring for 30 minutes. After the reaction mixture was washed with 50 ml of t-butylmethyl ether, the aqueous solution was adjusted to pH 3–4 by the addition of 1M hydrochloric acid, and extracted with ethyl acetate. The organic layer was washed with water and then with a saturated aqueous solution of sodium chloride, and dried over anhydrous magnesium sulfate. The solvent was distilled off under reduced pressure to obtain 3.3 g (102% yield) of the title compound.

$^1$H-NMR ($CDCl_3$) δ: 9.35 (br s, 1H), 7.31 (s, 5H), 4.50 (s, 2H), 3.53 (t, J=6.0 Hz, 2H), 2.48 (m, 2H), 1.87 (m, 2H); Mass, m/e: 194 ($M^+$), 91 (base).

(c) 4-Benzyloxybutyric Succinimide $^1$H-NMR ($CDCl_3$) δ: 7.32 (s, 5H), 4.52 (s, 2H), 3.56 (t, J=5.9 Hz, 2H), 2.79 (m, 2H), 2.07 (m, 2H); Mass, m/e: 193 ($M^+$ –Su), 91 (base).

(d) 5(3)-(3-Benzyloxypropyl)-3(5)-(4-fluorophenyl)-4-(4-pyridyl)pyrazole was Synthesized in Substantially the Same Manner as in Example 49

$^1$H-NMR ($CDCl_3$) δ: 8.53 (dd, J=1.7, 4.5 Hz, 2H), 7.15 (m, 9H), 4.54 (s, 2H), 3.55 (t, J=5.7 Hz, 2H), 2.84, (t-like, 2H), 1.97 (m, 2H); Mass, m/e: 387 ($M^+$), 91 (base).

(e) Synthesis of 3(5)-(4-Fluorophenyl)-5(3)-(3-hydroxypropyl)-4-(4-pyridyl)pyrazole 1.2 g of 5(3)-(3-benzyloxypropyl)-3(5)-(4-fluorophenyl)-4-(4-pyridyl)pyrazole, 22 ml of cyclohexene and 0.2 g of 20% palladium hydroxide were suspended in 100 ml of ethanol, followed by heating under reflux for 4 hours. After being allowed to cool, the reaction mixture was filtered through celite and the filtrate was evaporated to dryness under reduced pressure. The resulting crystals were washed with diethyl ether to obtain 0.8 g (91% yield) of the title compound.

$^1$H-NMR (DMSO-$d_6$) δ: 8.50 (dd, J=1.5, 4.4 Hz, 2H), 7.23 (m, 4H), 4.43 (br s, 1H), 3.40 (m, 2H), 2.61 (m, 2H), 1.70 (m, 2H); Mass, m/e: 297 ($M^+$), 252 (base).

(f) Synthesis of 3(5)-(4-Fluorophenyl)-5(3)-[3-(1-pyrazolyl)propyl]-4-(4-pyridyl)pyrazole 125 mg of 3(5)-(4-fluorophenyl)-5(3)-(3-hydroxypropyl)-4-(4-pyridyl)pyrazole and 0.06 ml of a 37% formaldehyde solution were dissolved in 5 ml of ethanol, and 0.07 ml of pyrrolidine was added thereto, followed by heating under reflux for 6 hours. The reaction mixture was concentrated under reduced pressure and extracted with ethyl acetate. This extract was washed with water and then with a saturated aqueous solution of sodium chloride, and dried over anhydrous sodium sulfate. Thereafter, the solvent was distilled off under reduced pressure to obtain 160 mg of a colorless viscous substance. While a solution containing this compound and 0.7 ml of diisopropylethylamine in 10 ml of tetrahydrofuran was being cooled with ice, 0.04 ml of methanesulfonyl chloride was added dropwise thereto, followed by stirring for 1.5 hours. After the reaction mixture was extracted with ether, this extract was washed with water and then with a saturated aqueous solution of sodium chloride, and dried over anhydrous sodium sulfate. Thereafter, the solvent was distilled off under reduced pressure and the resulting residue was dissolved in 5 ml of tetrahydrofuran. On the other hand, while a mixture composed of 25 mg of 60% sodium hydride and 5 ml of dimethylformamide was being cooled with ice, 31 mg of pyrazole was added thereto, followed by stirring at room temperature for 15 minutes. After this mixture was cooled with ice again, the aforesaid tetrahydrofuran solution was added dropwise thereto, followed by stirring at room temperature for 2 hours. After the reaction mixture was extracted with ethyl acetate, this extract was washed with water and then with a saturated aqueous solution of sodium chloride, and dried over sodium sulfate. Thereafter, the solvent was distilled off under reduced pressure and the resulting residue was purified by silica gel column chromatography using 30 g of silica gel [with an elution solvent comprising ethyl acetate-methanol (9:1)]. Thus, 71 mg (49% yield) of the title compound was obtained as a white solid material.

A white solid material; Melting point: 144.5–146.5° C.; $^1$H-NMR ($CDCl_3$) δ: 8.55 (dd, J=1.5, 4.4 Hz, 2H), 7.6–6.8 (m, 8H), 6.31 (dd, J=1.2, 2.1 Hz, 1H), 4.27 (t, J=6.3 Hz, 2H), 2.61 (t, J=6.8 Hz, 2H), 2.3–1.9 (m, 2H); IR (KBr) ν max: 2930, 1604, 1520, 1222, 838 $cm^{-1}$; Mass, m/e: 347 ($M^+$), 266 (base).

Example 56

Synthesis of 3-(4-Fluorophenyl)-1-methyl-5-[3-(4-nitrophenyl)propyl]-4-(4-pyridyl)pyrazole 20 mg of 60% sodium hydride was suspended in 5 ml of tetrahydrofuran, and a solution containing 191 mg of 3(5)-(4-fluorophenyl)-5(3)-[3-(4-nitrophenyl)propyl]-4-(4-pyridyl)pyrazole in 10 ml of tetrahydrofuran was added thereto, followed by stirring at room temperature for 1 hour. After the reaction mixture was cooled to −70° C., methyl iodide was added thereto, followed by stirring at the same temperature for 30 minutes. Then, the reaction mixture was gradually returned to room temperature and stirred for 1 hour. The reaction mixture was washed with a saturated aqueous solution of sodium hydrogen carbonate, dried over anhydrous magnesium sulfate, and concentrated. The resulting residue was purified by silica gel column chromatography [using 25 g of silica gel and an elution solvent comprising chloroform-methanol (100:1), and then 25 g of silica gel and an elution solvent comprising hexane-ethyl acetate-methanol (4:4:0.5)]. Thus, 87 mg (44% yield) of the title compound was obtained as a white powder.

Melting point: 129.1–131.8° C.; $^1$H-NMR ($CDCl_3$) δ: 8.55 (br d, J=5.7 Hz, 2H), 8.12 (m, 2H), 7.42–6.90 (m, 8H), 3.86 (s, 3H), 2.69 (br m, 4H), 1.95 (br m, 2H); IR (KBr) ν max: 1602, 1516, 1344 $cm^{-1}$; Mass, m/e: 416 ($M^+$), 266 (base).

Example 57

Synthesis of 5-[3-(4-Aminophenyl)propyl]-3-(4-fluorophenyl)-1-methyl-4-(4-pyridyl)pyrazole 45 mg of 5-[3-(4-nitrophenyl)propyl]-3-(4-fluorophenyl)-1-methyl-4-(4-pyridyl)pyrazole was dissolved in 6 ml of methanol, followed by the addition of 2 ml of cyclohexene.

Then, 45 mg of 10% palladium-carbon was added thereto, followed by heating under reflux for 2 hours. After the reaction mixture was filtered, the filtrated was concentrated to obtain 43 mg of the title compound quantitatively as a colorless amorphous substance.

Melting point: 80.5–81.1° C.; $^1$H-NMR (CD$_3$OD) δ: 8.31 (br d, J=7.0 Hz, 2H), 7.38–6.58 (m, 8H), 7.04 (dd, J=1.8, 6.4 Hz, 2H), 3.83 (s, 3H), 2.76–2.42 (m, 4H), 1.83 (m, 2H); IR (KBr) ν max: 3600–3200, 1604, 1516 cm$^{-1}$; Mass, m/e: 386 (M$^+$), 267 (base).

The compounds of the following Examples 58–60 were synthesized in substantially the same manner as in Example 56.

Example 58

3-(4-Fluorophenyl)-1-methyl-5-(3-phenylpropyl)-4-(4-pyridyl)pyrazole

A white solid material; Melting point: 83–87° C.; $^1$H-NMR (CDCl$_3$) δ: 8.50 (dd, J=1.5, 4.6 Hz, 2H), 7.5–6.8 (m, 11H), 3.83 (s, 3H), 2.8–2.4 (m, 4H), 2.1–1.5 (m, 2H); IR (KBr) ν max: 1596, 1522, 1444, 1218, 838 cm$^{-1}$; Mass, m/e: 371 (M$^+$), 267 (base).

Example 59

1-Methyl-3-(3,4-methylenedioxyphenyl)-5-(3-phenylpropyl)-4-(4-pyridyl)pyrazole

A white powder; $^1$H-NMR (CDCl$_3$) δ: 8.52 (dd, J=1.9, 4.4 Hz, 2H), 7.43–6.60 (m, 10H), 5.92 (s, 2H), 3.81 (s, 3H), 2.77–2.49 (m, 4H), 2.07–1.70 (m, 2H); IR (KBr) ν max: 2936, 1594, 1510, 1458, 1232 cm$^{-1}$; Mass, m/e: 397 (M$^+$, base).

Example 60

3-(3,4-Difluorophenyl)-1-methyl-5-(3-phenylpropyl)-4-(4-pyridyl)pyrazole $^1$H-NMR (CDCl$_3$) δ: 8.52 (dd, J=1.8, 4.4 Hz, 2H), 7.42–6.86 (m, 10H), 3.82 (s, 3H), 2.78–2.49 (m, 4H), 2.07–1.73 (m, 2H); IR (KBr) ν max: 2944, 1596, 1522, 1454 cm$^{-1}$; Mass, m/e: 389 (M$^+$), 285 (base).

Example 61

(a) Synthesis of 1-(2-Benzyloxyethyl)-3-(4-fluorophenyl)-5-(3-phenylpropyl)-4-(4-pyridyl) pyrazole and 1-(2-Benzyloxyethyl)-5-(4-fluorophenyl)-3-(3-phenylpropyl)-4-(4-pyridyl) pyrazole (a Mixture of Regioisomers)

298 mg of 3(5)-(4-fluorophenyl)-5(3)-(3-phenylpropyl)-4-(4-pyridyl)pyrazole was dissolved in 5 ml of dimethylformamide, and 40 mg of 60% sodium hydride was added thereto. After this mixture was stirred at room temperature for 40 minutes, a dimethylformamide solution (5 ml) containing 189 mg of 2-benzyloxyethyl methanesulfonate was added dropwise thereto, followed by stirring for 3 hours. After completion of the reaction, the reaction mixture was extracted with ethyl acetate. This extract was washed with water and a saturated aqueous solution of sodium hydrogen carbonate, and dried over magnesium sulfate. The solvent was distilled off under reduced pressure, and the resulting residue was purified by silica gel column chromatography using 30 g of silica gel [with an elution solvent comprising hexane-ethyl acetate (2:1)]. Thus, 312 mg (76% yield) of the title compound was obtained as a colorless viscous substance.

$^1$H-NMR (CDCl$_3$) δ: 8.49 (dd, J=1.7, 4.5 Hz, 0.7H), 8.39 (dd, J=1.5, 4.6 Hz, 0.3H), 7.4–6.8 (m, 16H), 4.57 (s, 0.3H), 4.48 (s, 0.7H), 4.45–3.6 (m, 4H), 2.8–2.4 (m, 4H), 2.1–1.7 (m, 2H); Mass, m/e: 491 (M$^+$), 91 (base).

(b) Synthesis of 3-(4-Fluorophenyl)-1-(2-hydroxyethyl)-5-(3-phenylpropyl)-4-(4-pyridyl) pyrazole and 5-(4-Fluorophenyl)-1-(2-hydroxyethyl)-3-(3-phenylpropyl)-4-(4-pyridyl) pyrazole (a Mixture of Regioisomers)

279 mg of 1-(2-benzyloxyethyl)-3-(4-fluorophenyl)-5-(3-phenylpropyl)-4-(4-pyridyl)pyrazole and 1-(2-benzyloxyethyl)-5-(4-fluorophenyl)-3-(3-phenylpropyl)-4-(4-pyridyl)pyrazole (a mixture of regioisomers) was dissolved in 10 ml of ethanol, and 5 ml of cyclohexene and 100 mg of palladium hydroxide-carbon (Pearlman catalyst) were added thereto, followed by heating under reflux. After 12 hours, 2 ml of cyclohexene and 80 mg of palladium hydroxide-carbon (Pearlman catalyst) were added, followed by heating under reflux for 8 hours. Then, the reaction mixture was filtered through celite and the solvent was distilled off under reduced pressure. The resulting residue was purified by silica gel column chromatography using 20 g of silica gel [with an elution solvent comprising hexane-ethyl acetate (1:1)]. Thus, 129 mg (56% yield) of the title compound was obtained as a colorless viscous substance.

A colorless viscous substance; $^1$H-NMR (CDCl$_3$) δ: 8.51 (dd, J=1.7, 4.4 Hz, 0.7H), 8.40 (dd, J=1.6, 4.5 Hz, 0.3H), 7.4–6.8 (m, 11H), 4.4–3.9 (m, 4H), 2.9–2.5 (m, 4H), 2.1–1.7 (m, 2H); Mass, m/e: 401 (M$^+$), 297 (base).

Example 62

3-(4-Fluorophenyl)-1-(2-dimethylaminoethyl)-5-(3-phenylpropyl)-4-(4-pyridyl)pyrazole and 5-(4-Fluorophenyl)-1-(2-dimethylaminoethyl)-3-(3-phenylpropyl)-4-(4-pyridyl)pyrazole (a Mixture of Regioisomers)

A colorless viscous substance; $^1$H-NMR (CDCl$_3$) δ: 8.49 (dd, J=1.6, 4.5 Hz, 0.7H), 8.36 (dd, J=1.6, 4.5 Hz, 0.3H), 7.4–6.8 (m, 11H), 4.3–3.9 (m, 2H), 3.0–1.6 (m, 6H), 2.3–1.6 (m, 8H); Mass, m/e: 358 (M$^+$ −70), 58 (base).

Example 63

Synthesis of 3(5)-(4-Fluorophenyl)-5(3)-(3-phenylpropyl)-4-(4-pyridyl)pyrazole 373 mg of 3(5)-(4-fluorophenyl)-5(3)-(1-hydroxy-3-phenylpropyl)-4-(4-pyridyl)pyrazole and 5 mg of TEMPO were dissolved in 4 ml of ethylene chloride, and 0.1 ml of an aqueous solution containing 5 mg of potassium bromide was added thereto. While this mixture was being stirred at 0° C. or below, a mixture composed of 2.4 ml of a saturated aqueous solution of sodium hydrogen carbonate and 2.4 ml of a 5% aqueous solution of sodium hypochlorite was added dropwise thereto. After this mixture was returned to room temperature, 4 ml of a 10% aqueous solution of sodium nitrite was added thereto, and the reaction mixture was extracted twice with 20 ml portions of ethyl acetate. The combined organic layer was washed with 10 ml of a saturated aqueous solution of sodium chloride and dried over anhydrous sodium sulfate. After the solvent was distilled off under reduced pressure, the resulting residue was recrystallized from ethyl acetate to obtain 228 mg (61% yield) of the title compound as a white powder.

Melting point: 249–251.5° C.; $^1$H-NMR (CDCl$_3$) δ: 8.58 (dd, J=1.5, 4.5 Hz, 2H), 7.5–6.8 (m, 11H), 3.3–2.8 (m, 4H); IR (KBr) ν max: 2930, 1682, 1606, 1508, 1234, 838 cm$^{-1}$; Mass, m/e: 371 (M$^+$, base).

The compound of the following Example 64 was synthesized in substantially the same manner as in Example 63.

Example 64

5(3)-[3-(2-Chlorophenyl)propionyl]-3(5)-(4-fluorophenyl)-4-(4-pyridyl)pyrazole

A white powder; Melting point: 212.1–213.7° C.; $^1$H-NMR (CDCl$_3$) δ: 8.60 (br d, J=5.7 Hz, 2H), 7.39–6.90 (m, 10H), 3.14 (m, 4H); IR (KBr) ν max: 1690, 1606, 1512 cm$^{-1}$; Mass, m/e: 405 (M$^+$), 370 (base).

Example 65

Synthesis of (R)-3(5)-(4-Fluorophenyl)-5(3)-(1-phenylethylaminocarbonyl)-4-(4-pyridyl)pyrazole (a) 967 mg of 3-(4-fluorophenyl)-4-(4-pyridyl)-1-(1-pyrrolidinomethyl)pyrazole was dissolved in 40 ml of tetrahydrofuran. While this solution was being stirred at −70° C. or below, 2.3 ml of a 1.54M solution of butyl lithium in hexane was added dropwise thereto. After the stirring was continued for 30 minutes, 0.44 ml of diethyl carbonate was added dropwise thereto. After this mixture was gradually returned to room temperature and stirred for 12 hours, 10 ml of 2M hydrochloric acid was added thereto. After 1 hour, the reaction mixture was alkalified with a saturated aqueous solution of sodium hydrogen carbonate and extracted twice with 60 ml portions of chloroform. The combined organic layer was washed with 15 ml of a saturated aqueous solution of sodium chloride and dried over anhydrous magnesium sulfate. After the solvent was distilled off under reduced pressure, the resulting residue was purified by silica gel column chromatography using 50 g of silica gel (with an elution solvent comprising ethyl acetate). Thus, 146 mg (16% yield) of 3(5)-ethoxycarbonyl-5(3)-(4-fluorophenyl)-4-(4-pyridyl)pyrazole was obtained as a white powder.

Melting point: 222.5–224.5° C.; $^1$H-NMR (DMSO-d$_6$) δ: 14.4–13.9 (bs, 1H), 8.52 (dd, J=1.8, 4.4 Hz, 2H), 7.5–7.0 (m, 6H), 4.17 (q, J=7.0 Hz, 2H), 1.13 (t, J=7.0 Hz, 3H); IR (KBr) ν max: 2810, 1720, 1608, 1524, 1210, 840 cm$^{-1}$; Mass, m/e: 311 (M$^+$), 209 (base).

(b) 106 mg of 3(5)-ethoxycarbonyl-5(3)-(4-fluorophenyl)-4-(4-pyridyl)pyrazole was dissolved in a mixture composed of 5 ml of ethanol and 5 ml of tetrahydrofuran. Then, 3 ml of a 1M aqueous solution of sodium hydroxide was added thereto, followed by stirring at 60° C. for 3 hours. The reaction mixture was concentrated under reduced pressure, diluted with 20 ml of water, and then neutralized with 3 ml of 1M hydrochloric acid. The precipitated crystals were collected by filtration to obtain 90 mg (93% yield) of 3(5)-carboxy-5(3)-(4-fluorophenyl)-4-(4-pyridyl)pyrazole as a white powder.

Melting point: 250° C. (decomp.); $^1$H-NMR (DMSO-d$_6$) δ: 8.51 (m, 2H), 7.4–7.0 (m, 6H); IR (KBr) ν max: 3180, 1650, 1526, 1222, 838 cm$^{-1}$; Mass, m/e: 283 (M$^+$), 209 (base).

(c) 142.8 mg of 5(3)-carboxy-3(5)-(4-fluorophenyl)-4-(4-pyridyl)pyrazole was dissolved in 5 ml of dimethylformamide. While this solution was being stirred under cooling with ice, 96.0 mg of 1-ethyl-3-(3-dimethylamino-propyl) carbodiimide hydrochloride, 77.6 mg of N-hydroxybenzotriazole monohydrate, and 61.1 mg of (R)-(+)-1-phenylethylamine were added thereto, followed by stirring at room temperature for 3 hours. After the addition of water, the reaction mixture was extracted with chloroform. After the organic layer was dried over anhydrous magnesium sulfate, the solvent was distilled off under reduced pressure. The resulting residue was washed with diethyl ether and then dried to obtain 137.0 mg of the title compound as white crystals.

Melting point: 296.5–299.2° C.; $^1$H-NMR (DMSO-d$_6$) δ: 13.73 (bs, 1H), 8.55 (m, 1H), 8.42 (d, J=6.2 Hz, 2H), 7.31–7.11 (m, 11H), 5.14–4.97 (m, 1H), 1.44 (d, J=6.8 Hz, 3H); IR (KBr) ν max: 3180, 1630, 1604, 1536, 1500, 1222 cm$^{-1}$; Mass, m/e: 386 (M$^+$), 120 (base).

The compounds of the following Examples 66–69 were synthesized in substantially the same manner as in Example 65.

Example 66

(S)-3(5)-(4-Fluorophenyl)-5(3)-(1-phenylethylaminocarbonyl)-4-(4-pyridyl)pyrazole Melting point: 296.7–299.3° C.; $^1$H-NMR (DMSO-d$_6$) δ: 13.74 (bs, 1H), 8.57 (m, 1H), 8.43 (dd, J=1.5, 4.5 Hz, 2H), 7.47–7.02 (m, 11H), 5.22–4.89 (m, 1H), 1.44 (d, J=7.0 Hz, 3H); IR (KBr) ν max: 3200, 1630, 1602, 1544, 1500, 1218 cm$^{-1}$; Mass, m/e: 386 (M$^+$), 120 (base).

Example 67

5(3)-(2-Chlorobenzylaminocarbonyl)-3(5)-(4-fluorophenyl)-4-(4-pyridyl)pyrazole

Melting point: 245.2–246.5° C.; $^1$H-NMR (DMSO-d$_6$) δ: 13.82 (bs, 1H), 8.74 (bt, J=5.9 Hz, 1H), 8.45 (dd, J=1.5, 4.6 Hz, 2H), 7.49–7.12 (m, 10H), 4.46 (d, J=5.9 Hz, 2H); IR (KBr) ν max: 3352, 1658, 1606, 1532, 1510, 1234 cm$^{-1}$; Mass, m/e: 406 (M$^+$), 371 (base).

Example 68

3(5)-Benzylaminocarbonyl-5(3)-(4-fluorophenyl)-4-(4-pyridyl)pyrazole

A white powder; Melting point: 255° C. (decomp.); $^1$H-NMR (DMSO-d$_6$) δ: 13.8–13.6 (bs, 1H), 8.8–8.6 (bs, 1H), 8.5–8.4 (m, 2H), 7.5–7.0 (m, 6H), 4.42 (s, 1H), 4.35 (s, 1H); IR (KBr) ν max: 3296, 2920, 1650, 1606, 1510, 1226, 960, 826 cm$^{-1}$; Mass, m/e: 372 (M$^+$), 106 (base).

Example 69

3-(4-Fluorophenyl)-5-(4-methoxybenzylaminocarbonyl)-1-methyl-4-(4-pyridyl)pyrazole White crystals; Melting point: 162.3–164.8° C.; $^1$H-NMR (CDCl$_3$) δ: 8.50 (dd, J=1.5, 4.4 Hz, 2H), 7.35–6.74 (m, 10H), 5.50 (br s, 1H), 4.37 (s, 1H), 4.30 (s, 1H), 4.19 (s, 3H), 3.79 (s, 3H); IR (KBr) ν max: 3280, 1634, 1604, 1514, 1252 cm$^{-1}$; Mass, m/e: 416 (M$^+$), 121 (base).

Example 70

Synthesis of 3(5)-(4-Fluorophenyl)-5(3)-(N-methyl-2-chlorobenzylaminocarbonyl)-4-(4-pyridyl) pyrazole 120 mg of 3(5)-(4-fluorophenyl)-4-(4-pyridyl)pyrazole-5 (3)-carboxylic acid, 80 mg of N-methyl-2- chlorobenzylamine, 89 mg of water-soluble carbodiimide hydrochloride (WSC.HCl) and 71 mg of 1-hydroxybenzotriazole monohydrate (HOBt.H$_2$O) were dissolved in 10 ml of tetrahydrofuran, and 47 mg of triethylamine was added thereto, followed by stirring at room temperature for 3 hours. After the addition of chloroform, the reaction mixture was washed with a saturated aqueous solution of sodium chloride, dried over anhydrous magnesium sulfate, and then concentrated. The resulting residue was purified by silica gel column chromatography using 20 g of silica gel [with an elution solvent comprising chloroform-methanol (100:1)]. Thus, 140 mg (78% yield) of the title compound was obtained as a white powder.

Melting point: 198.4–199.3° C.; $^1$H-NMR (CDCl$_3$) δ: 8.52 (m, 2H), 7.37–7.05 (m, 10H), 4.81 (m, 2H), 3.83 (s, 3H); IR (KBr) ν max: 3200–2500, 1728, 1628, 1512 cm$^{-1}$; Mass, m/e: 385 (M$^+$ −Cl), 125 (base).

The compounds of the following Examples 71–81 were synthesized in substantially the same manner as in Example 70.

Example 71

3(5)-(4-Fluorophenyl)-5(3)-(N-methyl-2-methoxybenzylaminocarbonyl)-4-(4-pyridyl)pyrazole Melting point: 214.8–215.6° C.; $^1$H-NMR (CDCl$_3$) δ: 8.45 (dd, J=1.5, 3.3 Hz, 2H), 7.41–6.87 (m, 10H), 4.67 (m, 2H), 3.74 (s, 3H), 2.81 (br s, 3H); IR (KBr) ν max: 3200–2500, 1606, 1494 cm$^{-1}$; Mass, m/e: 416 (M$^+$), 91 (base).

Example 72

3(5)-(4-Fluorophenyl)-5(3)-(N-methylbenzylaminocarbonyl)-4-(4-pyridyl)pyrazole

White crystals; Melting point: 231.5–232.6° C.; $^1$H-NMR (DMSO-d$_6$) δ: 13.70 (br s, 1H), 8.47–8.35 (m, 2H), 7.52–7.07 (m, 11H), 4.63 (br s, 1H), 4.53 (br s, 1H), 2.83 (br s, 1.5H), 2.76 (br s, 1.5H); IR (KBr) ν max: 3036, 1632, 1604, 1506, 1236 cm$^{-1}$; Mass, m/e: 386 (M$^+$), 120 (base).

Example 73

3(5)-(4-Fluorophenyl)-5(3)-(N-methyl-4-methoxybenzylaminocarbonyl)-4-(4-pyridyl)pyrazole White crystals; Melting point: 225.8–228.4° C.; $^1$H-NMR (DMSO-d$_6$) δ: 13.72 (br s, 1H), 8.51–8.37 (m, 2H), 7.49–6.75 (m, 10H), 4.55 (s, 1H), 4.40 (s, 1H), 3.75 (s, 1.5H), 3.72 (s, 1.5H), 2.81 (s, 1.5H), 2.73 (s, 1.5H); IR (KBr) ν max: 2836, 1624, 1606, 1512, 1242, 1224 cm$^{-1}$; Mass, m/e: 416 (M$^+$), 121 (base).

Example 74

5(3)-(N-Ethylbenzylaminocarbonyl)-3(5)-(4-fluorophenyl)-4-(4-pyridyl)pyrazole

White crystals; Melting point: 202.9–204.6° C.; $^1$H-NMR (DMSO-d$_6$) δ: 13.67 (br s, 1H), 8.49–8.29 (m, 2H), 7.50–7.05 (m, 1H), 4.64 (s, 2H), 4.44 (br s, 2H), 1.07–0.92 (m, 3H); IR (KBr) ν max: 3060, 1626, 1604, 1496, 1224 cm$^{-1}$; Mass, m/e: 400 (M$^+$), 91 (base).

Example 75

1-Ethyl-5-(N-methylbenzylaminocarbonyl)-3-(4-fluorophenyl)-4-(4-pyridyl)pyrazole Melting point: 148.0–149.3° C.; $^1$H-NMR (CDCl$_3$) δ: 8.63–8.30 (m, 2H), 7.50–6.90 (m, 11H), 4.85–4.00 (m, 4H), 2.95 (s, 1.2H), 2.50 (s, 1.8H), 1.55 (t, J=7.3 Hz, 1.2H), 1.53 (t, J=7.3 Hz, 1.8H); IR (KBr) ν max: 1644, 1605, 1449, 1218 cm$^{-1}$; Mass, m/e: 414 (M$^+$), 91 (base).

Example 76

1-Ethyl-5-(N-ethylbenzylaminocarbonyl)-3-(4-fluorophenyl)-4-(4-pyridyl)pyrazole

Melting point: 114.9–116.7° C.; $^1$H-NMR (CDCl$_3$) δ: 8.63–8.35 (m, 2H), 7.50–6.90 (m, 11H), 4.85–2.75 (m, 6H), 1.53 (t, J=7.3 Hz, 3H), 1.09 (t, J=7.3 Hz, 1.5H), 0.77 (t, J=7.3 Hz, 1.5H); IR (KBr) ν max: 1635, 1605, 1446, 1224 cm$^{-1}$; Mass, m/e: 428 (M$^+$), 91 base.

Example 77

3-(4-Fluorophenyl)-1-methyl-5-(N-methylbenzylaminocarbonyl)-4-(4-pyridyl)pyrazole Pale-yellow crystals; Melting point: 149.1–150.2° C.; $^1$H-NMR (CDCl$_3$) δ: 8.58–8.37 (m, 2H), 7.46–6.75 (m, 11H), 4.66 (br s, 2H), 3.97 (s, 2H), 3.88 (s, 1H), 2.97 (s, 2H), 2.52 (s, 1H); IR (KBr) ν max: 3036, 1624, 1604, 1524, 1448, 1216 cm$^{-1}$; Mass, m/e: 400 (M$^+$), 132 (base).

Example 78

5-(N-Ethylbenzylaminocarbonyl)-3-(4-fluorophenyl)-1-methyl-4-(4-pyridyl)pyrazole $^1$H-NMR (CDCl$_3$) δ: 8.58–8.39 (m, 2H), 7.46–6.73 (m, 11H), 3.94 (s, 2H), 3.83 (s, 3H), 1.10 (t, J=7.3 Hz, 1.5H), 0.80 (t, J=7.3 Hz, 1.5H); IR (nujol) ν max: 2728, 1644, 1606, 1310 cm$^{-1}$; Mass, m/e: 414 (M$^+$), 280 (base).

Example 79

3-(4-Fluorophenyl)-1-methyl-5-(N-methyl-4-methoxybenzylaminocarbonyl)-4-(4-pyridyl)pyrazole White crystals; Melting point: 150.1–152.6° C.; $^1$H-NMR (CDCl$_3$) δ: 8.59–8.37 (m, 2H), 7.45–6.66 (m, 10H), 4.61 (br s, 2H), 3.95 (s, 2H), 3.89 (s, 1H), 3.82 (s, 2H), 3.76 (s, 1H), 2.94 (s, 1H), 2.50 (s, 2H); IR (KBr) ν max: 2936, 1622, 1600, 1508, 1252, 1244 cm$^{-1}$; Mass, m/e: 430 (M$^+$), 121 (base).

Example 80

1-Ethyl-3-(4-fluorophenyl)-5-(N-methyl-2-pyridylmethylaminocarbonyl)-4-(4-pyridyl)pyrazole White crystals; Melting point: 144.4–146.8° C.; $^1$H-NMR (CDCl$_3$) δ: 8.56–8.39 (m, 3H), 7.77–6.62 (m, 9H), 4.76 (br s, 2H), 4.66–4.16 (m, 2H), 2.98 (s, 1H), 2.69 (s, 2H), 1.68–1.45 (m, 3H); IR (KBr) ν max: 2932, 1646, 1602, 1524, 1408, 1218 cm$^{-1}$; Mass, m/e: 415 (M$^+$), 93 (base).

Example 81

3-(4-Fluorophenyl)-1-(2-hydroxyethyl)-5-(N-methylbenzylaminocarbonyl)-4-(4-pyridyl)pyrazole White crystals; Melting point: 135.9–138.1° C.; $^1$H-NMR (CDCl$_3$) δ: 8.60–8.35 (m, 2H), 7.46–6.74 (m, 11H), 4.79–3.93 (m, 6H), 3.79–3.21 (br s, 1H), 2.94 (s, 1H), 2.48 (s, 2H); IR (KBr) ν max: 3196, 1632, 1606, 1446, 1224 cm$^{-1}$; Mass, m/e: 430 (M$^+$), 91 (base).

The compounds of the following Examples 82–85 were synthesized in substantially the same manner as in Example 49.

Example 82

5(3)-(Benzyloxymethyl)-3(5)-(4-fluorophenyl)-4-(4-pyridyl)pyrazole

Melting point: 177.6–180.2° C.; $^1$H-NMR (CDCl$_3$) δ: 8.52 (dd, J=1.4, 4.4 Hz, 2H), 7.42–7.02 (m, 9H), 7.14 (dd, J=1.4, 4.4 Hz, 2H), 4.61 (s, 2H), 4.58 (s, 2H); IR (KBr) ν max: 2920, 1606, 1516, 1240, 834 cm$^{-1}$; Mass, m/e: 359 (M$^+$), 252, 91 (base).

Example 83

5(3)-[1-(Benzyloxy)ethyl]-3(5)-(4-fluorophenyl)-4-(4-pyridyl)pyrazole

A colorless powder; Melting point: 169.2–173.5° C.; $^1$H-NMR (CDCl$_3$) δ: 8.54 (dd, J=1.8, 4.4 Hz, 2H), 7.45–6.89 (m, 9H), 7.09 (dd, J=1.8, 4.4 Hz, 2H), 4.70 (q, J=6.6 Hz, 2H), 4.48 (s, 1H), 4.40 (s, 1H), 1.52 (d, J=6.6 Hz, 3H); IR (KBr) ν max: 2900, 1604, 1518, 1220, 838 cm$^{-1}$; Mass, m/e: 373 (M$^+$), 266, 237, 91 (base).

Example 84

5-[1-(Benzyloxy)ethyl]-3-(4-fluorophenyl)-1-methyl-4-(4-pyridyl)pyrazole $^1$H-NMR (CDCl$_3$) δ: 8.52 (dd, J=1.6, 4.4 Hz, 2H), 7.41–6.91 (m, 9H), 7.00 (dd, J=1.7, 4.4 Hz, 2H), 4.62 (q, J=6.8 Hz, 1H), 4.38 (s, 1H), 4.30 (s, 1H), 4.08 (s, 3H), 1.59 (d, J=6.8 Hz, 3H); IR (KBr) ν max: 2940, 1604, 1446, 1220, 840 cm$^{-1}$; Mass, m/e: 387 (M$^+$), 281, 91 (base).

Example 85

3-(4-Fluorophenyl)-1-methyl-5-[1-(1-phenylethyloxy)ethyl]-4-(4-pyridyl)pyrazole $^1$H-NMR (CDCl$_3$) δ: 8.43 (dd, J=1.8, 4.4 Hz, 1H), 8.39 (dd, J=1.8, 4.4 Hz, 1H), 7.41–6.97 (m, 9H), 6.84 (dd, J=1.8, 4.2 Hz, 1H), 6.78 (dd, J=1.8, 4.2 Hz, 1H), 4.58–4.24 (m, 2H), 4.11 (s, 1.5H), 3.97 (s, 1.5H), 1.56–1.34 (m, 6H); IR (KBr) ν max: 2980, 1602, 1448, 1224, 840 cm$^{-1}$; Mass, m/e: 401 (M$^+$), 281, 105 (base).

Example 86

(a) 5(3)-(2-Benzyl-1,3-dioxolan-2-yl)methyl-3(5)-(4-fluorophenyl)-4-(4-pyridyl)pyrazole was Synthesized in Substantially the Same Manner as in Example 49

$^1$H-NMR (CDCl$_3$) δ: 8.39 (dd, J=1.5, 4.4 Hz, 2H), 7.34–6.97 (m, 9H), 7.00 (dd, J=1.6, 4.6 Hz, 2H), 4.00–3.66 (m, 4H), 3.11 (s, 2H), 2.70 (s, 2H); Mass, m/e: 415 (M$^+$), 338, 163 (base), 91.

(b) Synthesis of 3(5)-(4-Fluorophenyl)-5(3)-(2-oxo-3-phenylpropyl)-4-(4-pyridyl)pyrazole 110 mg of 5(3)-(2-benzyl-1,3-dioxolan-2-yl)methyl-3(5)-(4-fluorophenyl)-4-(4-pyridyl)pyrazole was dissolved in 10 ml of 3M hydrochloric acid, followed by heating under reflux for 3 hours. After the reaction mixture was returned to room temperature, it was neutralized with a saturated aqueous solution of sodium hydrogen carbonate, and extracted with 100 ml of ethyl acetate. After this extract was dried over magnesium sulfate, the solvent was distilled off under reduced pressure. The resulting residue was purified by silica gel column chromatography using 30 g of silica gel [with an elution solvent comprising ethyl acetate-hexane (1:1)]. Thus, 68 mg (71% yield) of the title compound was obtained as a colorless powder.

Melting point: 187.7–193.5° C.; $^1$H-NMR (CDCl$_3$) δ: 10.70 (br s, 1H), 8.49 (dd, J=1.5, 4.4 Hz, 2H), 7.61–7.00 (m, 9H), 6.93 (dd, J=1.8, 4.4 Hz, 2H), 3.84 (s, 2H), 3.78 (s, 2H); IR (KBr) ν max: 1710, 1604, 1512, 1228, 838 cm$^{-1}$; Mass, m/e: 371 (M$^+$), 252, 91 (base).

The compound of the following Example 87 was synthesized in substantially the same manner as in Example 86.

Example 87

3-(4-Fluorophenyl)-1-methyl-5-(2-oxo-3-phenylpropyl)-4-(4-pyridyl)pyrazole

Melting point: 148.1–151.0° C.; $^1$H-NMR (CDCl$_3$) δ: 8.47 (dd, J=1.7, 4.4 Hz, 2H), 7.42–7.01 (m, 9H), 6.93 (dd, J=1.8, 4.4 Hz, 2H), 3.77 (s, 2H), 3.70 (s, 2H), 3.68 (s, 3H); IR (KBr) ν max: 1710, 1604, 1520, 1216, 838 cm$^{-1}$; Mass, m/e: 385 (M$^+$), 266, 91 (base).

Example 88

Synthesis of 3(5)-(4-Fluorophenyl)-5(3)-(2-hydroxy-3-phenylpropyl)-4-4-pyridyl)pyrazole 48 mg of 3(5)-(4-fluorophenyl)-5(3)-(2-oxo-3-phenylpropyl)-4-(4-pyridyl)pyrazole was dissolved in 10 ml of tetrahydrofuran, and 10 mg of lithium aluminum hydride was added thereto, followed by stirring at room temperature for 1 hour. After the addition of 10 ml of a saturated aqueous solution of sodium hydrogen carbonate, the reaction mixture was extracted with 100 ml of ethyl acetate. After this extract was dried over magnesium sulfate, the solvent was distilled off under reduced pressure. The resulting residue was purified by silica gel column chromatography using 30 g of silica gel [with an elution solvent comprising ethyl acetate-hexane (2:1)]. Thus, 42 mg (89% yield) of the title compound was obtained as a colorless amorphous substance.

A colorless amorphous substance; $^1$H-NMR (CDCl$_3$) δ: 8.49 (dd, J=1.8, 4.4 Hz, 2H), 7.40–6.88 (m, 10H), 6.98 (dd, J=1.5, 4.4 Hz, 2H), 4.28–4.00 (m, 1H), 2.91–2.77 (m, 4H); IR (KBr) ν max: 3216, 1604, 1516, 1226, 838 cm$^{-1}$; Mass, m/e: 373 (M$^+$), 252 (base).

Example 89

Synthesis of 3(5)-(4-Fluorophenyl)-5(3)-(2-phenoxyethyl)-4-(4-pyridyl)pyrazole 322 mg of 3-(4-fluorophenyl)-4-(4-pyridyl)-1-(1-pyrrolidinomethyl)pyrazole was dissolved in 10 ml of tetrahydrofuran. While this solution was being stirred at −65° C. or below, 1.3 ml of a 1.54M solution of butyl lithium in hexane was added dropwise thereto. After the stirring was continued for 30 minutes, 5 ml of a tetrahydrofuran solution containing 402 mg of 2-phenoxyethyl bromide was added dropwise thereto. After this mixture was gradually returned to room temperature and stirred for 18 hours, 3 ml of 2M hydrochloric acid was added thereto. After 40 minutes, the reaction mixture was alkalified with a saturated aqueous solution of sodium hydrogen carbonate and extracted twice with 20 ml portions of ethyl acetate. The combined organic layer was washed with 5 ml of a saturated aqueous solution of sodium chloride and dried over anhydrous magnesium sulfate. After the solvent was distilled off under reduced pressure, the resulting residue was purified by silica gel column chromatography using 40 g of silica gel [with an elution solvent comprising hexane-ethyl acetate (1:1)]. Thus, 12 mg (3% yield) of the title compound was obtained as a white powder.

Melting point: 160–162° C.; $^1$H-NMR (CDCl$_3$) δ: 8.55 (dd, J=1.7, 4.4 Hz, 2H), 7.5–6.7 (m, 11H), 4.22 (t, J=6.0 Hz, 2H), 3.17 (t, J=6.0 Hz, 2H); IR (KBr) ν max: 2950, 1602, 1514, 1238, 836 cm$^{-1}$; Mass, m/e: 359 (M$^+$), 77 (base).

The compound of the following Example 90 was synthesized in substantially the same manner as in Example 89.

Example 90

3(5)-(4-Fluorophenyl)-5(3)-(3-oxo-3-phenylpropyl)-4-(4-pyridyl)pyrazole

Melting point: 140.2–141.4° C.; $^1$H-NMR (CDCl$_3$) δ: 8.48 (dd, J=1.5, 4.6 Hz, 2H), 8.03–6.92 (m, 11H), 4.66 (t, J=6.2 Hz, 2H), 3.66 (t, J=6.2 Hz, 2H); IR (KBr) ν max: 3450, 3050, 1678, 1602, 1524 cm$^{-1}$; Mass, m/e: 371 (M$^+$), 266 (base).

Example 91

3(5)-(4-Fluorophenyl)-5(3)-(3-hydroxy-3-phenylpropyl)-4-(4-pyridyl)pyrazole was Synthesized in Substantially the Same Manner as in Example 88

A colorless amorphous compound; $^1$H-NMR (CDCl$_3$) δ: 8.50 (dd, J=1.6, 4.4 Hz, 2H), 7.38–6.86 (m, 10H), 7.05 (dd, J=1.5, 4.4 Hz, 2H), 4.81 (t, 1H, J=6.3 Hz), 2.86 (t, 2H, J=6.6 Hz), 2.13 (t, 2H, J=6.6 Hz); IR (KBr) ν max: 3200, 1606, 1520, 1222, 836 cm$^{-1}$; Mass, m/e: 373 (M$^+$), 253 (base).

Example 92

(5)-(4-Fluorophenyl)-5(3)-[1-hydroxy-3-(2-pyridyl)-2-butenyl]-4-(4-pyridyl)pyrazole was Synthesized in Substantially the Same Manner as in Example 1

A colorless amorphous compound; $^1$H-NMR (CDCl$_3$) δ: 8.52 (dd, J=1.6, 4.5 Hz, 2H), 8.5–8.3 (m, 1H), 7.7–6.6 (m, 9H), 5.75 (d, J=8.8 Hz, 1H), 1.97 (d, J=1.1 Hz, 3H); IR (KBr) ν max: 3180, 1606, 1518, 1434, 1222, 838 cm$^{-1}$; Mass, m/e: 386 (M$^+$), 368 (base).

Example 93

3(5)-(4-Fluorophenyl)-4-(4-pyridyl)-5(3)-[N-(1,2,3,4-tetrahydroisoquinolinyl)carbonyl]pyrazole was Synthesized in Substantially the Same Manner as in Example 70

White crystals; Melting point: 234.2–236.7° C.; $^1$H-NMR (CDCl$_3$) δ: 8.39 (br s, 2H), 7.44–6.97 (m, 10H), 4.85 (br s, 1H), 4.40 (br s, 1H), 3.96–3.85 (m, 1H), 3.62–3.40 (m, 1H), 3.04–2.74 (m, 1H), 2.61–2.13 (m, 1H); IR (KBr) ν max: 2856, 1632, 1604, 1492, 1224 cm$^{-1}$; Mass, m/e: 398 (M$^+$), 132 (base).

Next, an example of a pharmaceutical preparation containing a compound in accordance with the present invention is given.

Preparation Example A: Tablets
Tablets:

|  | mg/tablet |
|---|---|
| Active ingredient | 30.0 |
| Starch | 5.0 |
| Lactose | 132.0 |
| Carboxymethylcellulose calcium | 15.0 |
| Talc | 1.0 |
| Magnesium stearate | 2.0 |
|  | 180.0 |

The active ingredient is pulverized to a particle size of 70 microns or less. Then, starch, lactose and carboxymethylcellulose calcium are added thereto and thoroughly mixed therewith. After the addition of 10% starch paste, the above powder mixture is agitated and blended to prepare granules. After drying, these granules are adjusted to a particle diameter of about 1,000 microns, and mixed with talc and magnesium stearate. The resulting mixture is formed into tablets.

What is claimed is:

1. A substituted pyrazole compound represented by the following formula, or a salt thereof

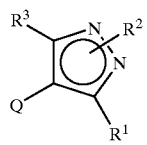

(I)

wherein:
R$^1$ represents a group of any one of the following formulae i) to vii):
i) —CH(OH)—CH(R$^4$)—(A)$_n$—Y
ii) —CH=C(R$^4$)—(A)$_n$—Y
iii) —CH$_2$—CH(R$^4$)—(A)$_n$—Y
iv) —CO—B$^1$—A—Y
v) —A—B$^2$—CH(R$^4$)—Y
vi) —A—CH(R$^4$)—B$^2$—Y
vii) —CH(OH)—CH=C(R$^4$)—Y
  in which A is —CH$_2$— or —CH(CH$_3$)—, Y is an aryl group which may optionally be substituted by halogen, lower alkyl, lower alkoxy, amino or nitro, or a cycloalkyl group, R$^4$ is a hydrogen atom or a lower alkyl group, B$^1$ is —CH(R$^4$)—, B$^2$ is —CH(OH)—, —CO— or —O—, and n is 1;
R$^2$ represents a hydrogen atom, a lower alkyl group which may optionally be substituted by hydroxyl, amino, or mono- or di-(lower alkyl)amino or an aralkyl group;
R$^3$ represents a phenyl group which may optionally be substituted by halogen, trifluoromethyl or lower alkylenedioxy, or a pyridyl group; and
Q represents a pyridyl group.

2. The substituted pyrazole compound or a salt thereof as claimed in claim 1 wherein R$^1$ is a group of the formula —CH$_2$—CH(R$^4$)—(A)$_n$—Y.

3. The substituted pyrazole compound or a salt thereof as claimed in claim 1 wherein Y is an unsubstituted phenyl group; a phenyl group substituted by 1 or 2 substituents selected from halogen, lower alkyl, lower alkoxy, amino and nitro; a phenyl group substituted by 3 to 5 halogen atoms or a cyclohexyl group.

4. The substituted pyrazole compound or a salt thereof as claimed in claim 3 wherein Y is a phenyl, 2-chlorophenyl, 4-fluorophenyl, 2-methylphenyl, 3-methylphenyl, 2-methoxyphenyl, 4-methoxyphenyl, 2-aminophenyl, 4-aminophenyl, 2-nitrophenyl, 4-nitrophenyl, 2-chloro-4-fluorophenyl, 4-amino-3-methylphenyl, 3-methyl-4-nitrophenyl, 2,3,4,5,6-pentafluorophenyl or cyclohexyl group.

5. The substituted pyrazole compound or a salt thereof as claimed in claim 1 wherein $R^4$ is a hydrogen atom or a methyl group.

6. The substituted pyrazole compound or a salt thereof as claimed in claim 1 wherein $R^2$ is a hydrogen atom or a methyl, ethyl, n-propyl, isopropyl, 2-hydroxyethyl or 2-dimethylaminoethyl group.

7. The substituted pyrazole compound or a salt thereof as claimed in claim 1 wherein $R^3$ is a 3-chlorophenyl, 4-fluorophenyl, 3-trifluoromethylphenyl, 3,4-dichlorophenyl, 3,4-difluorophenyl, 3-chloro-4-fluorophenyl, 3,4-methylenedioxyphenyl, 2-pyridyl, 3-pyridyl or 4-pyridyl group.

8. A pharmaceutical composition comprising an effective amount of a substituted pyrazole compound of formula (I) or a salt thereof as claimed in claim 1, and a pharmaceutically acceptable additive.

9. A pharmaceutical composition as claimed in claim 8, for inhibiting a p38MAP kinase.

10. A pharmaceutical composition as claimed in claim 8, for the treatment of tumor necrosis factor α-related diseases, interleukin 1-related diseases, interleukin 6-related diseases and cyclooxygenase II-related diseases.

11. The pharmaceutical composition as claimed in claim 10 wherein the tumor necrosis factor α-related diseases, interleukin 1-related diseases, interleukin 6-related diseases or cyclooxygenase II-related diseases include rheumatoid arthritis, multiple sclerosis, osteoarthritis, psoriasis, HIV, asthma, septic shock, IBD, Crohn's disease, Alzheimer's disease, diabetes, cachexia, osteoporosis, graft versus host disease, adult RDS, arteriosclerosis, gout, glomerulonephrtis, congestive heart failure, ulcerative colitis, sepsis, cerebral malaria, restenosis, hepatitis, SLE, thrombosis, born resorption disease, chronic pulmonary inflammation disease, cardiac reperfusion injury, renal reperfusion injury, cancer, Reiter's syndrome, preterm labor, eczema, allograft rejection, stroke, fever, Behcet's disease, neuralgia, meningitis, sunburn, contact dermatitis, acute synovitis, spondylitis, muscle degeneration, angiogenesis, conjunctivitis, psoriatic arthritis, viral myocarditis, pancreatitis, glioblastoma, bleeding, joint inflammation, endotoxic shock, parasitic infections, tuberculosis, myocardial infarction, leprosy, diabetic retinopathy, IBS, transplant rejection, burns, bronchitis, ischemic heart disease, eclampsia, pneumonia, remission of swelling, low back pain, laryngopharyngitis, Kawasaki disease, myelopathy or atopic dermatitis.

* * * * *